(12) United States Patent
Nozawa et al.

(10) Patent No.: US 7,264,935 B2
(45) Date of Patent: Sep. 4, 2007

(54) POTASSIUM-DEPENDENT SODIUM-CALCIUM EXCHANGER

(75) Inventors: Katsura Nozawa, Ibaraki (JP); Shinobu Mochizuki, Ibaraki (JP)

(73) Assignee: Astellas Pharma Inc., Tokyo (JP)

( * ) Notice: Subject to any disclaimer, the term of this patent is extended or adjusted under 35 U.S.C. 154(b) by 223 days.

(21) Appl. No.: 10/506,624

(22) PCT Filed: Jul. 31, 2003

(86) PCT No.: PCT/JP03/09732

§ 371 (c)(1),
(2), (4) Date: Sep. 3, 2004

(87) PCT Pub. No.: WO2004/013173

PCT Pub. Date: Feb. 12, 2004

(65) Prior Publication Data

US 2005/0119173 A1    Jun. 2, 2005

(30) Foreign Application Priority Data

Aug. 1, 2002 (JP) ............ 2002-225114
Jun. 26, 2003 (JP) ............ 2003-182989

(51) Int. Cl.
G01N 33/53 (2006.01)
C12P 21/02 (2006.01)
C12N 5/10 (2006.01)
C07K 14/435 (2006.01)
C07H 21/00 (2006.01)

(52) U.S. Cl. ............ 435/7.1; 536/23.5; 435/69.1; 435/252.3; 435/325; 435/320.1; 530/350

(58) Field of Classification Search ............ None
See application file for complete search history.

(56) References Cited

U.S. PATENT DOCUMENTS 6,787,352 B2 * 9/2004 Friddle et al. ............ 435/325

FOREIGN PATENT DOCUMENTS

| JP | 9-67336 | 3/1997 |
|---|---|---|
| WO | 97/09306 | 3/1997 |
| WO | WO 01/83512 A1 | 11/2001 |
| WO | 02/26980 A2 | 4/2002 |

OTHER PUBLICATIONS

Balasubramanyam M et al. Na+/Ca2+ exchange-mediated calcium entry in human lymphocytes. J Clin Invest, 1994; 94: 2002-2008.*
Harada N et al. Adenosine and selective A2A receptor agonists reduce ischemia/reperfusion injury of rat liver mainly by inhibiting leukocyte activation. J Pharm Exp Therap. 2000; 294(3): 1034-1042.*
Mochizuki S and Jiang C. Na+/Ca2+ exchanger and myocardial ischemia/reperfusion. Japanese Heart J, 1998; 39(6): 707-714.*
Siegl et al.; "Inhibition of Na$^+$/Ca$^{2+}$Exchange in Membrane Vesicle and Papillary Muscle Preparations From Guinea Pig Heart by Analogs of Amiloride"; Proc. Natl. Acad. Sci. USA, vol. 81, pp. 3238-3242, (1984).
International Preliminary Examination Report for application PCT/JP2003/009732 filed Jul. 31, 2003.
EPO Communication and Supplementary Partial European Search Report mailed Nov. 8, 2005, for application EP 03 76 6674.
Li et al., "Molecular Cloning of a Fourth Member of the Potassium-dependent Sodium-Calcium Exchanger Gene Family, NCKX4," Journal of Biological Chemistry, 277(50):48410-48417 (2002).

* cited by examiner

*Primary Examiner*—Elizabeth Kemmerer
*Assistant Examiner*—Kimberly A. Ballard
(74) *Attorney, Agent, or Firm*—Finnegan, Henderson, Farabow, Garrett & Dunner, L.L.P.

(57) ABSTRACT

A novel polypeptide, a polynucleotide encoding the polypeptide, an expression vector comprising the polynucleotide, a cell transfected by the expression vector, a method for producing the polypeptide, and a convenient screening system for obtaining a substance useful in treating cell injuries due to postischemic reperfusion or an inflammatory disease, are disclosed.

The polypeptide is a potassium-dependent sodium-calcium exchanger expressed in peripheral leukocytes.

10 Claims, No Drawings

POTASSIUM-DEPENDENT SODIUM-CALCIUM EXCHANGER

TECHNICAL FIELD

This invention relates to a potassium-dependent sodium-calcium exchanger useful in screening an agent for treating a cell injury due to postischemic reperfusion and/or an inflammatory disease.

BACKGROUND ART

During ischemia, an organ proceeds via a reversible to the irreversible phase of cell injury. It is considered that an injury can be avoided if the organ is reperfused in the process, but experimental and clinical examinations point out that the reperfusion per se newly damages the organ. This is called a reperfusion injury. It is known that both free radicals generated during reperfusion and excess intracellular calcium (calcium overload) due to reperfusion play an important role in the generation of reperfusion injuries (non-patent references 1 and 2). Regarding the mechanism of the calcium overload, several hypotheses are proposed, as follows (non-patent reference 3):

(1) Due to a failure of an energy-dependent calcium exchange system, calcium flows into cells in accordance with a concentration gradient thereof.
(2) A concentration of intracellular sodium ions is increased during ischemia, and therefore calcium flows into cells via a sodium-calcium exchange system.
(3) An increased α receptor density during ischemia promotes a calcium overload after reperfusion.
(4) Due to a severe failure of a cell membrane, extracellular calcium flows into cells in accordance with a concentration gradient thereof.

Further, it is considered that, in delayed neuronal cell death during postischemic reperfusion in the brain, a glutamate receptor, NMDA (N-methyl-D-aspartate) receptor, is activated, an NMDA activated calcium channel is opened, and thus calcium flows into cells (non-patent reference 4).

After transient ischemia in an experimental animal, the phenomenon of no reflow (when a blood flow is reflowed, a region where a blood flow is not topically reflowed is generated) is observed in the brain, heart, and kidney. As major mechanisms of the phenomenon of no reflow, hemorrhage and destruction of microvascular construction (for example, capillary embolus by leukocytes, or swelling of vascular endothelial cells), platelet thrombosis, or the like are suggested (non-patent reference 5). As cells which block microvessels in a focus of middle cerebral artery occlusion, polymorphonuclear leucocytes, monocytes, or platelets are observed in addition to erythrocytes, and particularly, capillary embolus by neutrophils classified into leukocytes is noted as a cause of the phenomenon of no reflow (non-patent reference 5). When passing through microvessels, polymorphonuclear leucocytes delay an erythrocyte flow. Further, during ischemia in the brain, polymorphonuclear leucocytes interact with vascular endothelial cells or platelets, and expressions of receptors for adhesion factors are increased at the surfaces of polynuclear leucocytes. Furthermore, monoclonal antibodies against adhesion factors such as L-selection, CD11, CD18, or ICAM-1 attenuated leukocyte accumulation and reduced the area of infarction, and thus it was suggested that the expression of adhesion factors plays an important role in accumulation of leukocytes during postischemic reperfusion (non-patent references 6 and 7). In addition, it is reported that the expression of adhesion factors in leukocytes is increased by increasing an intracellular calcium concentration (non-patent reference 8).

Numerous ion channels controlling an intracellular ion environment are known. As those which play a particularly important role in postischemic reperfusion injury, for example, a sodium-hydrogen exchanger and a sodium-calcium exchanger are known. During the process of postischemic reperfusion injury, there are two stages in the passage from ischemia to reperfusion. One is ischemia and the other is reperfusion. During ischemia, blood is not supplied and an anaerobic condition is brought about, and thus an exhaustion of energy, promotion of anaerobic metabolism, accumulation of harmful metabolites, and the like occur, and, as a result, acidosis proceeds. During reperfusion, oxygen is supplied, and thus acidosis is attenuated, together with a supply of energy, restart of aerobic metabolism, and removal of accumulated metabolites, to return the physiological conditions. However, because injury proceeds rapidly during reperfusion, it seems that the conditions neutralized by reperfusion are worse than that of acidosis by ischemia. It is known that the sodium-hydrogen exchanger and the sodium-calcium exchanger are involved in this phenomenon (non-patent reference 9).

It is known that the sodium-hydrogen exchanger exists on the cell membrane, is involved in a control of intracellular pH, and has an activity of extruding hydrogen ions outside the cell in accordance with a concentration gradient during acidosis, and simultaneously, incorporating sodium ions into the cell. It is reported that the mechanism in which an expression and activity of the sodium-hydrogen exchanger are suppressed during ischemic preconditioning is involved in a protective action (non-patent reference 10). Further, it is reported that the activation of the sodium-hydrogen exchanger activates neutrophils and promotes neutrophil adhesion via expression of CD11, CD18, or ICAM-1 (non-patent reference 11).

There are two types of sodium-calcium exchange reactions, i.e., the classic sodium-calcium exchange reaction and the potassium-dependent sodium-calcium exchange reaction (non-patent references 12 and 13). It is considered that sodium-calcium exchangers exist in all tissues. The physiological function is an extrusion of intracellular calcium outside the cell, accompanied by an influx of extracellular sodium. Further, it is reported that the reverse reaction in which intracellular sodium is extruded and calcium flows into the cell may occur physiologically.

According to a report about ion dynamics during postischemic reperfusion, oxygen is not supplied and anaerobic metabolism is promoted during ischemia, and thus the substrate (ATP) for energy is exhausted and acidosis proceeds. That is, sodium ions are not extruded outside the cell due to the inactivation of sodium pumps, and sodium ions flow into the cell by gradually extruding hydrogen ions outside the cell via the sodium-hydrogen exchanger for an adjustment of acidosis. The accumulation of intracellular sodium ions results in an increase in intracellular calcium ions via the sodium-calcium exchanger. Further, because the pH around tissues is neutralized rapidly during reperfusion, a concentration gradient between intracellular hydrogen ions accumulated by anaerobic metabolism and decreased hydrogen ions therearound becomes large. In addition, the sodium-hydrogen exchanger is activated, and then hydrogen ions are extruded outside the cell and sodium ions rapidly flow into the cell. After the rapid influx of sodium ions, the sodium-calcium exchanger is activated, and then sodium ions are extruded outside the cell and calcium ions are transported into the cell. That is, a concentration of intracellular calcium is increased rapidly to become a calcium overload. This rapidly increased pH and calcium influx into the cell is considered to be a trigger for injurious actions occuring during postischemic reperfusion (non-patent reference 9). As described above, the activation of the sodium-hydrogen exchanger as the first step, and the activation of the sodium-calcium exchanger as the second step, play an important role in a relatively early stage of postischemic reperfusion injury.

In connection with the increased intracellular calcium concentration in leukocytes during postischemic reperfusion, it is known that a calcium influx into the cell is important in the process of neutrophil activation caused by leukocyte mobilizing factors such as formylmethionyl-leucinyl-phenylalanine (fMLP), arachidonic acid, or leukotoriene B4, and that the neutrophil activation is inhibited by suppressing the influx (non-patent reference 14). Further, it is reported that intracellular pH is increased by treatment with fMLP, and that inhibitors of the sodium-hydrogen exchanger suppressed increased intracellular pH and leukocyte migration (non-patent reference 15).

However, it is not known whether the inhibition of the sodium-calcium exchanger in leukocytes suppresses leukocyte activation, and a sodium-calcium exchanger which triggers leukocyte activation which causes postischemic reperfusion injury and/or inflammation has not been identified until now.

Patent reference 1 discloses a sequence consisting of 603 amino acids as that of a human sodium/calcium exchanger. Non-patent reference 16 discloses a sequence of potassium-dependent sodium-calcium exchanger gene NCKX3 which encodes 644 amino acids and is most abundant in the brain, with highest levels in thalamic nuclei, hippocampal CA1 neurons, and layer IV of the cerebral cortex. Patent reference 2 discloses a sequence of a human diagnostic protein consisting of 480 amino acids. Patent reference 3 discloses sequences of human secretory proteins consisting of 235 and 169 amino acids.

(non-patent reference 1) "Circulation", (U.S.A.), 1990, 82, p. 723-738
(non-patent reference 2) "Annual Review of Physiology", (U.S.A.), 1992, 54, p. 243-256
(non-patent reference 3) "Kokyu To Junkan", 2001, 49(1), p. 5-11
(non-patent reference 4) "CLINICAL NEUROSCIENCE", (U.S.A.), 1999, 17(5), p. 567-569
(non-patent reference 5) "Kokyu To Junkan", 2001, 49(1), p. 13-20
(non-patent reference 6) "Circulation", (U.S.A.), 1993, 88, p. 649-658
(non-patent reference 7) "American Journal of Pathology", (U.S.A.), 1993, 143, p. 410-418
(non-patent reference 8) "Cell Adhesion & Communication", (Switzerland), 1993, 1, p. 21-32
(non-patent reference 9) Yasuo Morishita et al., "Zoki no Kyoketsu-saikanryu-shogai-Kiso to Rinsyo (Reperfusion Injury)", SHINDAN-TO-CHIRYOSHA, 2002, p.1-225
(non-patent reference 10) "Circulation Research", (U.S.A.), 1999, 85, p. 723-730
(non-patent reference 11) "Journal of Cardiovascular Pharmacology", (U.S.A.), 2001, 37, p. 668-677
(non-patent reference 12) "Tanpakushitsu Kakusan Koso", 1998, 43(12), p. 1555-1560
(non-patent reference 13) "Journal of Biological Chemistry", (U.S.A.), 1993, 268, p. 6874-6877
(non-patent reference 14) "Biochemical & Biophysical Research Communications)], (U.S.A.), 1981, 103, p. 227-232
(non-patent reference 15) "British Journal of Pharmacology", (United Kingdom), 1998, 124, p. 627-638
(non-patent reference 16) "Journal of Biological Chemistry", (U.S.A.), 2001, 276, p. 23161
(patent reference 1) WO02/26980
(patent reference 2) WO01/75067
(patent reference 3) WO00/43495

DISCLOSURE OF INVENTION

As described in BACKGROUND ART, with respect to the leukocyte activation, postischemic reperfusion and inflammation have common aspects, such as an increased intracellular pH in leukocytes and activation of the sodium-hydrogen exchanger thereby, and an increased intracellular calcium concentration thereby. It is considered that the sodium-calcium exchanger in leukocytes is involved in leukocyte activation during postischemic reperfusion injury and inflammation. That is, it is considered that an inhibition of sodium-calcium exchanger activation in leukocytes suppresses the increased intracellular calcium concentration in leukocytes and inhibits the leukocyte activation.

The object of the present invention is to provide a novel potassium-dependent sodium-calcium exchanger in leukocytes, and a novel polynucleotide encoding the polypeptide, and further to provide a convenient screening system for obtaining a substance useful as a therapeutic agent for cell injury due to postischemic reperfusion or an inflammatory disease, of which the therapeutic effect is achieved by inhibiting an activation of leukocytes.

The present inventors conducted intensive studies and, as a result, obtained polynucleotides encoding potassium-dependent sodium-calcium exchangers consisting of the amino acid sequences of SEQ ID NOS: 2 and 4, respectively, and abundantly expressed in leukocytes; prepared cells expressing each polypeptide; and provided screening tools for obtaining a substance useful as an inhibitor of the sodium-calcium exchangers, that is, a therapeutic agent for postischemic reperfusion injury or an inflammatory disease. Further, the present inventors constructed systems for detecting the sodium-calcium exchange activity by using the cells expressing each sodium-calcium exchanger; and provided a method for screening a substance useful as a therapeutic agent for postischemic reperfusion injury and an inflammatory disease, on the basis of inhibition of the above activity. Furthermore, the present inventors obtained inhibitors of the sodium-calcium exchangers by the above screening method; confirmed that the inhibitors inhibited migration of human peripheral polymorphonuclear leukocytes, that is, activation of leukocytes; and provided novel therapeutic agents for postischemic reperfusion injury and/or an inflammatory disease containing each inhibitor of leukocyte activation; and thus the present invention was completed.

The present invention relates to:

[1] (1) a polypeptide consisting of the amino acid sequence of SEQ ID NO: 2 or SEQ ID NO: 4, or (2) a polypeptide exhibiting a potassium-dependent sodium-calcium exchange activity and consisting of an amino acid sequence in which 1 to 5 amino acids in total are substituted, deleted, inserted, and/or added at one or plural portions in the amino acid sequence of SEQ ID NO: 2 or SEQ ID NO: 4;

[2] the polypeptide of [1], which is (a) a polypeptide consisting of the amino acid sequence of SEQ ID NO: 2, or (2) a polypeptide exhibiting a potassium-dependent sodium-calcium exchange activity and consisting of an amino acid sequence in which 1 to 5 amino acids in total are substituted, deleted, inserted, and/or added at one or plural portions in the amino acid sequence of SEQ ID NO: 2;

[3] the polypeptide of [1] or [2], the sodium-calcium exchange activity is a reverse sodium-calcium exchange activity;

[4] a polynucleotide encoding the polypeptide of [1] to [3];

[5] an expression vector comprising the polynucleotide of [4];

[6] a cell transfected with the expression vector of [5];

[7] a method for producing the polypeptide of [1] to [3], characterized by using the cell of [6];

[8] a method for screening an inhibitor of the polypeptide of [1] to [3], comprising the steps of:
(1) bringing a cell expressing the polypeptide into contact with a substance to be tested,
(2) analyzing whether or not a potassium-dependent sodium-calcium exchange activity in the polypeptide is inhibited, and
(3) selecting a substance which inhibits the potassium-dependent sodium-calcium exchange activity in the polypeptide;

[9] a method for screening an inhibitor of leukocyte activation, comprising the steps of:
(1) bringing a cell expressing the polypeptide of [1] to [3] into contact with a substance to be tested,
(2) analyzing whether or not a potassium-dependent sodium-calcium exchange activity in the polypeptide is inhibited, and
(3) selecting a substance which inhibits the potassium-dependent sodium-calcium exchange activity in the polypeptide;

[10] a method for screening a therapeutic agent for postischemic reperfusion injury and/or an inflammatory disease, comprising the steps of:
(1) bringing a cell expressing the polypeptide of [1] to [3] into contact with a substance to be tested,
(2) analyzing whether or not a potassium-dependent sodium-calcium exchange activity in the polypeptide is inhibited, and
(3) selecting a substance which inhibits the potassium-dependent sodium-calcium exchange activity in the polypeptide;

[11] a process for manufacturing a pharmaceutical composition for treating postischemic reperfusion injury and/or an inflammatory disease, comprising the steps of:
(1) bringing a cell expressing the polypeptide of [1] to [3] into contact with a substance to be tested,
(2) analyzing whether or not a potassium-dependent sodium-calcium exchange activity in the polypeptide is inhibited, and
(3) preparing a medicament containing the substance;

[12] a pharmaceutical composition for inhibiting leukocyte activation, comprising as an active ingredient a substance obtainable by the method of [8];

[13] a pharmaceutical composition for treating postischemic reperfusion injury and/or an inflammatory disease, comprising as an active ingredient a substance obtainable by the method of [8];

[14] a method for inhibiting leukocyte activation, comprising the step of:
administering to a subject a substance obtainable by the method [8];

[15] a method for treating postischemic reperfusion injury and/or an inflammatory disease, comprising the step of:
administering to a subject a substance obtainable by the method of [8];

[16] use of a substance obtainable by the method of [8], in the manufacture of a pharmaceutical composition for inhibiting leukocyte activation; and

[17] use of a substance obtainable by the method of [8], in the manufacture of a pharmaceutical composition for treating postischemic reperfusion injury and/or an inflammatory disease.

The present invention includes use of the cell expressing the polypeptide of [1] to [3] in screening an inhibitor of leukocyte activation or a therapeutic agent for postischemic reperfusion injury and/or an inflammatory disease.

The term "therapeutic agent for postischemic reperfusion injury" or "pharmaceutical composition for treating postischemic reperfusion injury" as used herein includes both an agent or pharmaceutical composition used for treating a patient suffering postischemic reperfusion injury and that preventively used for a subject having the risk of postischemic reperfusion injury. The term "therapeutic agent for an inflammatory disease" or "pharmaceutical composition for treating an inflammatory disease" as used herein includes both an agent or pharmaceutical composition used for treating a patient suffering an inflammatory disease and that preventively used for a subject having the risk of an inflammatory disease.

WO02/26980 discloses the amino acid sequence identical with that, consisting of 603 amino acids, of SEQ ID NO: 4 in the present application, but does not disclose that a polypeptide consisting of the above amino acid sequence or a polypeptide encoding the polypeptide was actually obtained and does not disclose a specific method for obtaining the same. Therefore, the polypeptide consisting of the amino acid sequence of SEQ ID NO: 4 and the polynucleotide encoding the polypeptide were first provided by the present inventors.

Further, WO01/75067 discloses a human diagnostic protein (480 amino acids) in which the amino acid sequence consisting of the 35th to 480th amino acids therein has a 82% homology with that consisting of the 257th to 622nd amino acids in the amino acid sequence of SEQ ID NO: 2 in the present application and has a 77% homology with that consisting of the 257th to 603rd amino acids in the amino acid sequence of SEQ ID NO: 4 in the present application. WO00/43495 discloses a human secretory protein (235 amino acids) and a human secretory protein (169 amino acids) in which the amino acid sequences consisting of the 33rd to 235th amino acids and the 1st to 169th amino acids have 86% and 97% homologies with those consisting of the 400th to 603rd amino acids and the 435th to 603rd amino acids in the amino acid sequence of SEQ ID NO: 4 in the present application, respectively. J. Biol. Chem., 276, 23161, 2001 discloses NCKX3 (644 amino acids) in which the amino acid sequence consisting of the 17th to 641st amino acids therein has a 58% homology with that consisting of the 13th to 618th amino acids in the amino acid sequence of SEQ ID NO: 2 in the present application and has a 58% homology with that consisting of the 13th to 599th amino acids in the amino acid sequence of SEQ ID NO: 4 in the present application. However, to obtain a polypeptide useful in screening a therapeutic agent for cell injury due to postischemic reperfusion and/or an inflammatory disease, no references suggest an obtaining of the polypeptide of the present invention. Further, the polypeptide of the present invention has an advantageous effect which cannot be expected from the above known polypeptides, that is, a usefulness as a screening tool for obtaining an inhibitor of leukocyte activation (particularly a therapeutic agent for cell injury due to postischemic reperfusion and/or an inflammatory disease).

BEST MODE FOR CARRYING OUT THE INVENTION

The present invention will be explained in detail hereinafter.

1. Polypeptide, Polynucleotide, Expression Vector, and Cell of the Present Invention The polypeptide of the present invention includes (1) a polypeptide consisting of the amino acid sequence of SEQ ID NO: 2 or 4; and (2) a polypeptide consisting of an amino acid sequence in which 1 to 5 amino acids in total are substituted, deleted, inserted, and/or added at one or plural portions in the amino acid sequence of SEQ ID NO: 2 or 4, and exhibiting a potassium-dependent sodium-calcium exchange activity (preferably a reverse sodium-calcium exchange activity) (hereinafter referred to as a variation functionally equivalent). As the polypeptide of the present invention, the polypeptide consisting of the amino acid sequence of SEQ ID NO: 2 or 4 is preferable.

The term "exhibiting a sodium-calcium exchange activity" as used herein means exhibiting an exchange reaction in which intracellular sodium is extruded outside the cell and extracellular calcium flows into the cell (the reverse direction), or exhibiting an exchange reaction in which intracellular calcium is extruded outside the cell and extracellular sodium flows into the cell (the forward direction). Further, the term "exhibiting a reverse sodium-calcium exchange activity" as used herein means exhibiting an exchange reaction in which intracellular sodium is extruded outside the cell and extracellular calcium flows into the cell ($Na^+_i$-$Ca^{2+}_o$ exchange; the reverse direction). The term "exhibiting a forward sodium-calcium exchange activity" as used herein means exhibiting an exchange reaction in which intracellular calcium is extruded outside the cell and extracellular sodium flows into the cell ($Na^+_o$-$Ca^{2+}_i$ exchange; the forward direction).

Whether or not a polypeptide (hereinafter referred to as a test polypeptide) "exhibits a sodium-calcium exchange activity" may be confirmed by a method known to those skilled in the art (Iwamoto T. et al., J. Biol. Chem., 271, 22391-22397, 19962). A method for confirming it is not particularly limited and, for example, the following method may be used.

Cells are transfected with an expression vector comprising a polynucleotide encoding the test polypeptide. In the case of confirming the reverse sodium-calcium exchange activity, preferably a method described in Example 4 may be used. More particularly, the resulting cells are treated with an ionophore (such as monensin) to a univalent cation, to incorporate sodium into the cells; the extracellular solution is changed to a solution containing $^{45}Ca$, to exchange intracellular sodium for extracellular calcium; and an intracellular $^{45}Ca$ radioactivity is measured. In the case of confirming the forward sodium-calcium exchange activity, the resulting cells are cultured in a medium containing calcium chloride ($^{45}Ca$ chloride) to incorporate calcium ions into the cells; the cells are washed with a washing solution to remove calcium ions not incorporated; the extracellular solution is changed to an extracellular solution for measurement containing sodium ions; and a $^{45}Ca$ radioactivity contained in the solution is measured. When the radioactivity is detected, it may be confirmed that the test polypeptide "exhibits a sodium-calcium exchange activity".

As the polypeptide of the present invention, a polypeptide in which a radioactivity of two or more times that obtained in the case of the extracellular solution containing 150 mmol/L NaCl is detected when using the method of Example 4 is preferable.

Whether or not the sodium-calcium exchange activity of the test compound is "potassium-dependent" may be confirmed by a method known to those skilled in the art (Kimura, M., J. Biol. Chem., 268, p.6874-6877, 1993; Kraev A. et al., J. Biol. Chem., 276, 23161-23172, 2001). A method for confirming it is not particularly limited but, for example, the following method (preferably a method described in Example 4) may be used. More particularly, cells are transfected with an expression vector comprising a polynucleotide encoding the test polypeptide. When measuring the sodium-calcium exchange activity of the resulting cells, a $K^+$ concentration in the extracellular solution is varied, and an intracellular $^{45}Ca$ radioactivity in each $K^+$ concentration is measured. When a higher sodium-calcium exchange activity is detected in the presence of $K^+$, it may be confirmed that the sodium-calcium exchange activity of the test compound is "potassium-dependent".

As the polypeptide of the present invention, a polypeptide in which a radioactivity of five or more times that obtained in the case of the extracellular solution A described in Example 4 is detected when using the extracellular solution C or D described in Example 4 is preferable.

The polypeptides consisting of the amino acid sequences of SEQ ID NOS: 2 and 4, which are included in the polypeptide of the present invention, are novel human potassium-dependent sodium-calcium exchangers consisting of 622 and 603 amino acid residues, respectively. Each polypeptide consisting of the amino acid sequence of SEQ ID NO: 2 or 4 is expressed in peripheral leukocytes, as shown in Example 2.

The variation functionally equivalent of the present invention is not particularly limited, so long as it is a polypeptide consisting of an amino acid sequence in which 1 to 5 amino acids, preferably 1 to 3 amino acids, in total are substituted, deleted, inserted, and/or added at one or plural positions (for example, 1 to 3 positions) in the amino acid sequence of SEQ ID NO: 2 or 4, and exhibiting the potassium-dependent sodium-calcium exchange activity. Further, an origin of the variation functionally equivalent is not limited to a human.

The variation functionally equivalent of the present invention includes, for example, not only human variations of the polypeptide consisting of the amino acid sequence of SEQ ID NO: 2 or 4, but also variations functionally equivalent derived from organisms other than a human (such as a mouse, a hamster, or a dog). Further, it includes polypeptides prepared using polynucleotides obtained by artificially modifying their amino acid sequences encoded thereby by genetic engineering techniques, on the basis of polynucleotides encoding these native polypeptides (i.e., human variations or variations functionally equivalent derived from organisms other than a human), or on the basis of polynucleotides encoding the amino acid sequence of SEQ ID NO: 2 or 4. The term "variation" as used herein means an individual difference between the same polypeptides in the same species or a difference between homologous polypeptides in several species.

The variation functionally equivalent derived from a human or organisms other than a human may be obtained by those skilled in the art in accordance with the information of the base sequence of SEQ ID NO: 1 or 3 (for example, the sequence consisting of the 14th to 1882nd bases in the base sequence of SEQ ID NO: 1, or the sequence consisting of the 14th to 1825th bases in the base sequence of SEQ ID NO: 3). For example, an appropriate probe or appropriate primers are designed in accordance with the information of the base sequence. A polymerase chain reaction (PCR) method (Saiki, R. K. et al., Science, 239, 487-491, 1988) or a hybridization method is carried out using a sample (for example, total RNA or an mRNA fraction, a cDNA library, or a phage library) prepared from an organism (for example, a mammal such as a human, a mouse, a hamster, or a dog) of interest and the primers or the probe to obtain a polynucleotide encoding the polypeptide. A desired polypeptide may be obtained by expressing the resulting polynucleotide in an appropriate expression system, and then, for example, by confirming that the expressed polypeptide exhibits the sodium-calcium exchange activity by a method described in Example 4, and further confirming that the activity is dependent on a potassium ion by a method described in Example 4. In this connection, genetic engineering techniques may be performed in accordance with known methods (for example, Maniatis, T. et al., "Molecular Cloning—A Laboratory Manual", Cold Spring Harbor Laboratory, NY, 1982), unless otherwise specified.

Further, the above artificially-modified polypeptide using a polynucleotide modified artificially by genetic engineering techniques may be obtained by, for example, the following procedure. A polynucleotide encoding the polypeptide is obtained by a conventional method such as site-specific mutagenesis (Mark, D. F. et al., Proc. Natl. Acad. Sci. USA, 81, 5662-5666, 1984). A desired polypeptide may be obtained by expressing the resulting polynucleotide in an appropriate expression system, and then, for example, by confirming that the expressed polypeptide exhibits the sodium-calcium exchange activity by a method described in Example 4, and further confirming that the activity is dependent on a potassium ion by a method described in Example 4.

The polynucleotide of the present invention is not particularly limited, so long as it encodes the polypeptide of the present invention. As the polynucleotide of the present invention, there may be mentioned, for example, a polynucleotide having the sequence consisting of the 14th to 1882nd bases in the base sequence of SEQ ID NO: 1, or the sequence consisting of the 14th to 1825th bases in the base sequence of SEQ ID NO: 3. In this connection, the term "polynucleotide" as used herein includes both DNA and RNA.

A method for producing the polynucleotide of the present invention is not particularly limited, but there may be mentioned, for example, (1) a method using PCR, (2) a method using conventional genetic engineering techniques (i.e., a method for selecting a transformant comprising a desired cDNA from strains transformed with a cDNA library), or (3) a chemical synthesis method, as described in WO02/052000. These methods will be explained in this order hereinafter.

In the method using PCR, the polynucleotide of the present invention may be produced, for example, by the following procedure.

mRNA is extracted from human cells or tissue capable of producing the polypeptide of the present invention. A pair of primers, between which full-length mRNA corresponding to the polypeptide of the present invention or a partial region of the mRNA is located, is synthesized on the basis of the base sequence of a polynucleotide encoding the polypeptide of the present invention. Full-length cDNA encoding the polypeptide of the present invention or a part of the cDNA may be obtained by performing a reverse transcriptase-polymerase chain reaction (RT-PCR) using the extracted mRNA as a template. Further, a desired DNA fragment may be obtained by digesting the obtained DNA with a restriction enzyme or the like and performing ligation, if desired.

In the method using conventional genetic engineering techniques, the polynucleotide of the present invention may be produced, for example, by the following procedure.

First, single-stranded cDNA is synthesized by using reverse transcriptase from mRNA prepared by the above-mentioned PCR method as a template, and then double-stranded cDNA is synthesized from the single-stranded cDNA.

Next, a recombinant plasmid comprising the double-stranded cDNA is prepared and introduced into an *Escherichia coli* strain, such as DH 5α, thereby transforming the strain. A transformant is selected using a drug resistance against, for example, tetracycline or ampicillin as a marker. As a method for selecting a transformant containing the cDNA of interest from the resulting transformants, various methods, such as a method for screening a transformant using a synthetic oligonucleotide probe or a method for screening a transformant using a probe produced by PCR, may be used.

A method for collecting the polynucleotide of the present invention from the resulting transformant of interest can be carried out in accordance with a known method (for example, Maniatis, T. et al., "Molecular Cloning—A Laboratory Manual", Cold Spring Harbor Laboratory, NY, 1982). For example, it may be carried out by separating a fraction corresponding to the plasmid DNA from cells and cutting out the cDNA region from the plasmid DNA.

In the chemical synthesis method, the polynucleotide of the present invention may be produced, for example, by binding DNA fragments produced by a chemical synthesis method. Each DNA fragment can be synthesized using a DNA synthesizer [for example, Oligo 1000M DNA Synthesizer (Beckman) or 394 DNA/RNA Synthesizer (Applied Biosystems)].

In this connection, codons for each amino acid are known and can be optionally selected and determined by the conventional method, for example, by taking a codon usage of each host to be used into consideration (Crantham, R. et al., Nucleic Acids Res., 9, r43-r74, 1981). Further, a partial modification of codons of these base sequences can be carried out in accordance with a conventional method, such as site specific mutagenesis using a primer comprised of a synthetic oligonucleotide encoding for a desired modification (Mark, D. F. et al., Proc. Natl. Acad. Sci. USA, 81, 5662-5666, 1984).

Determination of the DNA sequences obtained by the above-mentioned methods can be carried out by, for example, a dideoxynucleotide chain termination method (Messing, J. and Vieira, J., Gene, 19, 269-276, 1982). For example, fluorescence labeled dideoxynucleotides are incorporated to a DNA fragment by a PCR method using a reaction solution containing fluorescence labeled dideoxynucleotides. The amplified DNA fragment is electrophoresed in a sequencer (for example, 3700DNA sequencer; PE Biosystems) and the base sequence thereof can be determined by detecting the fluorescence.

The isolated polynucleotide of the present invention is re-integrated into an appropriate vector DNA and a host cell (including a eucaryotic host cell and a procaryotic host cell)

may be transformed by the resulting expression vector. Further, it is possible to express the polynucleotide in a desired host cell, by introducing an appropriate promoter and a sequence related to the gene expression into the vector.

The expression vector of the present invention is not particularly limited, so long as it comprises the polynucleotide of the present invention. As the expression vector, there may be mentioned, for example, an expression vector obtained by introducing the polynucleotide of the present invention into a known expression vector appropriately selected in accordance with a host cell to be used.

The cell of the present invention is not particularly limited, so long as it is transfected with the expression vector of the present invention and comprises the polynucleotide of the present invention. The cell of the present invention may be, for example, a cell in which the polynucleotide is integrated into a chromosome of a host cell, or a cell containing the polynucleotide as an expression vector comprising the polynucleotide. Further, the cell of the present invention may be a cell expressing the polypeptide of the present invention, or a cell not expressing the polypeptide of the present invention. The cell of the present invention may be obtained by, for example, transfecting a desired host cell with the expression vector of the present invention.

In the eucaryotic host cells, for example, cells of vertebrates, insects, and yeast are included. As the vertebral cell, there may be mentioned, for example, a simian COS cell (Gluzman, Y., Cell, 23, 175-182, 1981), a dihydrofolate reductase defective strain of a Chinese hamster ovary cell (CHO-dhfr⁻ cell) (Urlaub, G. and Chasin, L. A., Proc. Natl. Acad. Sci. USA, 77, 4216-4220, 1980), a Chinese hamster lung fibroblast (Dede cell, ATCC: CCL-39) used in Example 4, a human fetal kidney derived HEK293 cell (ATCC: CRL-1573) used in Example 4, a 293-EBNA cell (Invitrogen) obtained by introducing an EBNA-1 gene of Epstein Barr Virus into HEK293 cell, or L929 cell (ATCC: CRL-2148).

As an expression vector for a vertebral cell, a vector containing a promoter positioned upstream of the gene to be expressed, an RNA splicing site, a polyadenylation site, a transcription termination sequence, and the like may be generally used. The vector may further contain a replication origin, if necessary. As the expression vector, there may be mentioned, for example, pSV2dhfr containing an SV40 early promoter (Subramani, S. et al., Mol. Cell. Biol., 1, 854-864, 1981), pEF-BOS containing a human elongation factor promoter (Mizushima, S. and Nagata, S., Nucleic Acids Res., 18, 5322, 1990), pCEP4 containing a cytomegalovirus promoter (Invitrogen), pIRESneo2 (CLONTECH), or pcDNA3.1 (Invitrogen).

When the COS cell is used as the host cell, a vector which has an SV40 replication origin, can perform an autonomous replication in the COS cell, and has a transcription promoter, a transcription termination signal, and an RNA splicing site, may be used as the expression vector. As the vector, there may be mentioned, for example, pME18S (Maruyama, K. and Takebe, Y., Med. Immunol., 20, 27-32, 1990), pEF-BOS (Mizushima, S. and Nagata, S., Nucleic Acids Res., 18, 5322, 1990), or pCDM8 (Seed, B., Nature, 329, 840-842, 1987).

The expression vector may be incorporated into COS cells by, for example, a DEAE-dextran method (Luthman, H. and Magnusson, G., Nucleic Acids Res., 11, 1295-1308, 1983), a calcium phosphate-DNA co-precipitation method (Graham, F. L. and van der Ed, A. J., Virology, 52, 456-457, 1973), a method using a commercially available transfection reagent (for example, FuGENE™6 Transfection Reagent; Roche Diagnostics), or an electroporation method (Neumann, E. et al., EMBO J., 1, 841-845, 1982).

When the CHO cell is used as the host cell, a transformant capable of stably producing the polypeptide of the present invention can be obtained by carrying out a co-transfection of an expression vector comprising the polynucleotide of the present invention, together with a vector capable of expressing a neo gene which functions as a G418 resistance marker, such as pRSVneo (Sambrook, J. et al., "Molecular Cloning—A Laboratory Manual", Cold Spring Harbor Laboratory, NY, 1989) or pSV2-neo (Southern, P. J. and Berg, P., J. Mol. Appl. Genet., 1, 327-341, 1982), and selecting a G418 resistant colony.

When the 293-EBNA cell is used as the host cell, for example, pCEP4 (Invitrogen) containing a replication origin of Epstein Barr Virus and capable of performing an autonomous replication in the 293-EBNA cell may be used as the expression vector.

The cell of the present invention may be cultured in accordance with the conventional method, and the polypeptide of the present invention is produced at the surface of the cell. As a medium to be used in the culturing, a medium commonly used in a desired host cell may be appropriately selected. In the case of the COS cell or Dede cell, for example, a medium such as an RPMI-1640 medium or a Dulbecco's modified Eagle's minimum essential medium (DMEM) may be used, by supplementing it with a serum component such as fetal bovine serum (FBS) if necessary. In the case of the 293-EBNA cell, a medium such as a Dulbecco's modified Eagle's minimum essential medium (DMEM) with a serum component such as fetal bovine serum (FBS) and G418 may be used.

The polypeptide of the present invention produced at the cell surface by culturing the cell of the present invention may be separated and purified therefrom by various known separation techniques making use of the physical properties, chemical properties and the like of the polypeptide. More particularly, a cell membrane fraction containing the polypeptide of the present invention may be obtained by culturing cells expressing the polypeptide of the present invention, suspending them in a buffer, homogenizing them, and centrifuging the resulting homogenate. After the obtained cell membrane fraction was solubilized, the polypeptide of the present invention may be purified by a commonly used treatment, for example, a treatment with a protein precipitant, ultrafiltration, various liquid. chromatography techniques such as molecular sieve chromatography (gel filtration), adsorption chromatography, ion exchange chromatography, affinity chromatography, or high performance liquid chromatography (HPLC), or dialysis, or a combination thereof.

2. Screening of Therapeutic Agents for Cell Injury Due to Postischemic Reperfusion and an Inflammatory Disease A substance which inhibits the polypeptide of the present invention can be screened by using the cell expressing the polypeptide of the present invention so as to exhibit the potassium-dependent sodium-calcium exchange activity.

As described in BACKGROUND ART, it is known that the intracellular calcium overload due to reperfusion plays an important role in the generation of a reperfusion injury and that the potassium-dependent sodium-calcium exchanger is involved in the calcium influx into the cell accompanied by the extrusion of intracellular sodium (reverse direction). Further, it is known that the sodium-calcium exchanger extrudes intracellular sodium outside the cell and incorporates calcium into the cell during postischemic reperfusion, to return the intracellular sodium overload caused by reperfusion to the original state. Furthermore, it is known that an expression of adhesive factors in leukocytes was increased by an increased intracellular calcium concentration, and that monoclonal antibodies against the adhesive factors suppressed the leukocyte accumulation and reduced the area of infarction. Therefore, it is considered that an inhibition of an intracellular calcium overload in leukocytes suppresses the leukocyte accumulation and leukocyte activation by adhesive factors due to the overload, and has an activity of avoiding cell injury caused by the phenomenon of no reflow.

The polypeptide of the present invention consisting of the sequence of SEQ ID NO: 2 or 4 is a potassium-dependent sodium-calcium exchanger expressed abundantly in peripheral leukocytes. Therefore, it is considered that an agent inhibiting or suppressing the potassium-dependent sodium-calcium exchange (reverse direction) in the polypeptide of the present invention suppresses calcium influx into the cell and inhibits the leukocyte activation or adhesion, and thus is useful in the treatment of a cell injury due to postischemic reperfusion.

Further, with respect to the leukocyte activation, postischemic reperfusion and inflammation have common aspects, such as an increased intracellular pH in leukocytes and activation of the sodium-hydrogen exchanger thereby, and an increased intracellular calcium concentration thereby, and thus it is considered that the sodium-calcium exchanger in leukocytes is involved in a leukocyte activation during postischemic reperfusion injury and inflammation. That is, it is considered that an inhibition of sodium-calcium exchanger activation in leukocytes suppresses the increased intracellular calcium concentration in leukocytes and inhibits the leukocyte activation.

Therefore, the cell of the present invention per se may be used as a screening tool for an inhibitor of the polypeptide of the present invention and an inhibitor of leukocyte activation (particularly a therapeutic agent for cell injury due to postischemic reperfusion and/or an inflammatory disease).

The term "inhibiting or suppressing the polypeptide of the present invention" means inhibiting or suppressing the potassium-dependent sodium-calcium exchange activity, including the case of inhibiting or suppressing the potassium-dependent sodium-calcium exchange activity by inhibiting or suppressing the expression of the polypeptide.

The method for screening an inhibitor of the polypeptide of the present invention and an inhibitor of leukocyte activation (particularly a therapeutic agent for cell injury due to postischemic reperfusion and/or an inflammatory disease) comprises the steps of:
bringing the cell of the present invention into contact with a substance to be tested,
analyzing whether or not the potassium-dependent sodium-calcium exchange activity in the polypeptide is inhibited, and
selecting a substance which inhibits the potassium-dependent sodium-calcium exchange activity in the polypeptide.

Substances to be tested which may be applied to the screening method of the present invention are not particularly limited, but there may be mentioned, for example, various known compounds (including peptides) registered in chemical files, compounds obtained by combinatorial chemistry techniques (Terrett, N. K. et al., Tetrahedron, 51, 8135-8137, 1995), or random peptides prepared by employing a phage display method (Felici, F. et al., J. Mol. Biol., 222, 301-310, 1991) or the like. In addition, culture supernatants of microorganisms, natural components derived from plants or marine organisms, or animal tissue extracts may be used as the test substances for screening. Further, compounds (including peptides) obtained by chemically or biologically modifying compounds (including peptides) selected by the screening method of the present invention may be used.

The screening method of the present invention is not particularly limited, so long as it comprises the steps of:
bringing a cell expressing the polypeptide of the present invention so as to function as the potassium-dependent sodium-calcium exchanger (i.e., including a cell which was transfected with an expression vector comprising a polynucleotide encoding the polypeptide of the present invention and expresses the polypeptide so as to function as the potassium-dependent sodium-calcium exchanger, and a naturally occurring cell which expresses the polypeptide of the present invention so as to function as the potassium-dependent sodium-calcium exchanger) into contact with a substance to be tested, (2) analyzing whether or not the potassium-dependent sodium-calcium exchange activity in the polypeptide is inhibited, and (3) selecting a substance which inhibits the potassium-dependent sodium-calcium exchange activity in the polypeptide. There may be mentioned, on the basis of differences in methods used for analyzing the inhibition of the polypeptide of the present invention, for example,

[1] a screening method utilizing a radioisotope $^{45}Ca^{2+}$ ion uptake, or

[2] a screening method utilizing a calcium sensitive dye.

Among these methods, the screening method utilizing a radioisotope $45Ca^{2+}$ ion uptake is preferable. As the cell used in the screening, the cell of the present invention prepared by transfecting it with an expression vector comprising a polynucleotide encoding the polypeptide of the present invention is preferable.

According to the above method [1], a substance which inhibits the polypeptide of the present invention and is useful in treating cell injury due to postischemic reperfusion and/or an inflammatory disease may be screened by, for example, the following method. Sodium is incorporated into cells expressing the polypeptide of the present invention at the cell surface, using an ionophore (such as monensin) to a univalent cation; the extracellular solution is changed to a radioisotope $^{45}Ca^{2+}$ ion-containing extracellular solution with or without a test compound; and an intracellular $^{45}Ca^{2+}$ radioactivity is measured. Then, whether or not the polypeptide of the present invention is inhibited is analyzed, on the basis of the difference in amounts of radioactivity incorporated into cells in the presence or absence of the test substance. That is, the screening method [1] of the present invention comprises the steps of:
incorporating radioisotope $45Ca^{2+}$ ions into the cell expressing the polypeptide of the present invention at the cell surface, and simultaneously, bringing the cell into contact with a substance to be tested, and
detecting an amount of radioactivity incorporated into the cell.

For example, the cells expressing the polypeptide of the present invention are treated with an extracellular solution containing a test compound and monensin, to incorporate sodium into the cells. The extracellular solution is changed to an extracellular solution containing the test compound and $^{45}Ca^{2+}$, to incorporate $^{45}Ca^{2+}$ into the cells by the sodium-calcium exchange activity. The cells are washed with a solution containing lanthanum, an inhibitor of the sodium-calcium exchange activity, to remove $^{45}Ca^{2+}$ not incorporated. When the reverse sodium-calcium exchange activity is inhibited, an amount of 45Ca$^{2+}$ influx into the cells is decreased, and thus whether or not the polypeptide of the present invention is inhibited can be analyzed on the basis of the radioactivity in the cells as an indicator of the reverse sodium-calcium exchange activity. More particularly, it is preferable to detect the reverse sodium-calcium exchange activity by the method described in Example 4. An inhibitor of the polypeptide of the present invention can be screened by analyzing a change of radioactivity incorporated into the cells by adding the test substance.

When screening a substance which inhibits the polypeptide of the present invention and is useful in treating a cell injury due to postischemic reperfusion and/or an inflammatory disease, by the above method [2], for example, a calcium sensitive dye is incorporated into the cells expressing the polypeptide of the present invention at the cell surface, and then whether or not the polypeptide of the present invention is inhibited is analyzed, on the basis of a change of a fluorescence intensity thereof in the cells in the presence or absence of the test compound. That is, in the screening method [2] of the present invention, the cells expressing the polypeptide of the present invention at the cell surface are treated with an extracellular solution containing an ionophore (such as monensin) to a univalent cation, to incorporate sodium into the cells. The extracellular solution is changed to an extracellular solution containing a test compound and a calcium sensitive dye, to incorporate the calcium sensitive dye into the cells by the sodium-calcium exchange activity. The cells are washed with a solution containing an inhibitor of the sodium-calcium exchange activity such as lanthanum, to remove the calcium sensitive dye not incorporated. When the reverse sodium-calcium exchange activity is inhibited, a fluorescence intensity of the calcium sensitive dye in the cells is decreased, and thus whether or not the polypeptide of the present invention is inhibited can be analyzed, on the basis of the fluorescence intensity in the cells as an indicator of the reverse sodium-calcium exchange activity. An inhibitor of the polypeptide of the present invention can be screened by detecting the fluorescence intensity of the calcium sensitive dye in the presence of the test compound.

The screening method comprises the steps of:
incorporating a calcium sensitive dye into the cell, and then
bringing the cell into contact with a substance to be tested, and
detecting the fluorescence intensity of the calcium sensitive dye in the cell. This screening utilizes the feature that a calcium sensitive dye can optically detect calcium influx accompanied by the reverse-mode activation of sodium-calcium exchanger.

More particularly, the activity of the polypeptide of the present invention can be detected using, for example, Fura-2 or a derivative thereof as the calcium sensitive dye. An inhibitor of the polypeptide of the present invention can be screened by comparing a change of the fluorescence intensity of the dye in the presence or absence of the test substance. When the reverse sodium-calcium exchange activity is inhibited, the fluorescence intensity is decreased.

As described above, according to the screening method of the present invention, a substance (particularly a compound) which inhibits the potassium-dependent sodium-calcium exchange activity of the polypeptide of the present invention, i.e., a substance (particularly a compound) having an inhibitory activity, can be screened. A compound having an inhibitory activity to be selected in the screening method of the present invention may be defined as a compound which inhibits an activity of the novel potassium-dependent sodium-calcium exchanger consisting of the amino acid sequence of SEQ ID NO: 2 or 4. As the compound, a compound having IC50 of 100 µmol/L or less is preferable. For example, when a test compound is reacted for a predetermined period under the conditions described in Example 6, a compound having IC50 of 100 µmol/L or less can be selected as a substance having an inhibitory activity. Using an inhibitory compound isolated by the screening as a main component, a medicament which targets the novel potassium-dependent sodium-calcium exchanger consisting of the amino acid sequence of SEQ ID NO: 2 or 4 can be obtained. For example, IC50 of 2-[2-[4-(4-nitrobenzyloxy) phenyl]ethyl]isothiourea methanesulfonate (hereinafter referred to as compound A) selected in Example 6 were 15.8 µmol/L and 35.0 µmol/L, with respect to the novel potassium-dependent sodium-calcium exchangers consisting of the amino acid sequences of SEQ ID NOS: 2 and 4, respectively. Further, IC50 of 3',4'-dichlorobenzamil (hereinafter referred to as compound B) were 20.2 µmol/L and 58.9 µmol/L, with respect to the novel potassium-dependent sodium-calcium exchangers consisting of the amino acid sequences of SEQ ID NOS: 2 and 4, respectively. From the results, it is apparent that an inhibitor of the novel potassium-dependent sodium-calcium exchanger consisting of the amino acid sequence of SEQ ID NO: 2 or 4 can be selected by the screening method of the present invention.

3. Medicament of the Present Invention

The medicament of the present invention comprising, as an active ingredient, a compound (preferably the above compound A or B) which modifies an activity of the novel potassium-dependent sodium-calcium exchanger consisting of the amino acid sequence of SEQ ID NO: 2 or 4 may be prepared using carriers, fillers, or other additives generally used in the preparation of medicaments, in accordance with the active ingredient.

Examples of administration include oral administration by tablets, pills, capsules, granules, fine granules, powders, oral solutions and the like, and parenteral administration by injections (e.g., intravenous, intramuscular, or the like), suppositories, transdermal preparations, transmucosal absorption preparations and the like. Particularly, in the case of peptides which are digested in the stomach, a parenteral administration such as an intravenous injection or the like is preferable.

In the solid composition of the present invention for use in the oral administration, one or more active substances may be mixed with at least one inert diluent such as lactose, mannitol, glucose, microcrystalline cellulose, hydroxypropylcellulose, starch, polyvinyl pyrrolidone, or aluminum magnesium silicate. In the usual way, the composition may contain additives other than the inert diluent, such as a lubricant, a disintegrating agent, a stabilizing agent, or a solubilizing or solubilization assisting agent. If necessary, tablets or pills may be coated with a sugar coating or a film of a gastric or enteric substance.

The liquid composition for oral administration may include, for example, emulsions, solutions, suspensions, syrups, and elixirs, and may contain a generally used inert diluent such as purified water or ethyl alcohol. The composition may contain additives other than the inert diluent, such as moistening agents, suspending agents, sweeteners, flavors, or antiseptics.

The injections for parenteral administration may include aseptic aqueous or non-aqueous solutions, suspensions, and emulsions. Examples of the diluent for use in the aqueous solutions and suspensions include distilled water for injection use and physiological saline. Examples of the diluent for use in the non-aqueous solutions and suspensions include alcohols (e.g., ethanol), glycols (e.g., propylene glycol or polyethylene glycol), polysorbate 80 (trade name) and the like. Such a composition may further contain a moistening agent, an emulsifying agent, a dispersing agent, a stabilizing agent, a solubilizing or solubilization assisting agent, an antiseptic or the like. These compositions may be sterilized, for example, by filtration through a bacteria retaining filter, blending of a germicide, or irradiation. Alternatively, they may be used by first making them into sterile solid compositions and dissolving them in sterile water or other sterile solvent for injection use prior to their use.

The dose is optionally decided by taking into consideration the strength of each active ingredient selected by the aforementioned screening method, or symptoms, age, sex, or the like of each patient to be administered. For example, in the case of oral administration, the usual dosage for an adult (60 kg in weight) is about 0.1 to 100 mg, preferably 0.1 to 50 mg per day. In the case of parenteral administration, the usual dosage is about 0.01 to 50 mg, preferably 0.01 to 10 mg per day in the form of an injection.

EXAMPLES

The present invention now will be further illustrated by, but is by no means limited to, the following Examples. The procedures were performed in accordance with the known methods (for example, Maniatis, T., et al., "Molecular Cloning—A Laboratory Manual", Cold Spring Harbor Laboratory, NY, 1982; and Hille, B., Ionic Channels of Excitable Membranes, 2nd Ed., Sinauer Associates Inc., MA, 1992), unless otherwise specified.

Example 1

Isolation of Genes Ecoding Novel Potassium-Dependent Sodium-Calcium Exchangers and Construction of Expression Vectors A full-length cDNA encoding each novel sodium-calcium exchanger of the present invention having the amino acid sequence of SEQ ID NO: 2 or 4 was obtained by a reverse transcriptase-polymerase chain reaction (RT-PCR) method using human brain cDNA (Marathon-Ready cDNA; Clontech) as a template, by the following procedure.

A PCR was carried out using human brain cDNA (Marathon-Ready cDNA; Clontech) as a template, an oligonucleotide consisting of the base sequence of SEQ ID NO: 5 (having the EcoRI recognition sequence added to the 5'-terminus) as a forward primer, an oligonucleotide consisting of the base sequence of SEQ ID NO: 6 (having the KpnI recognition sequence added to the 5'-terminus) as a reverse primer, and DNA Polymerase (PLATINUM Taq DNA Polymerase High-Fidelity; GIBCO-BRL). In the PCR, a thermal denaturation was first performed at 95° C. for 1 minute, and then a cycle consisting of reactions at 98° C. for 10 seconds, at 60° C. for 20 seconds, and at 68° C. for 3 minutes was repeated 40 times. As a result, two DNA bands of approximately 1.9 kbp were amplified. The longer DNA fragment was designated "622" and the shorter one was designated "603".

Each DNA fragment was digested with restriction enzymes EcoRI and KpnI, and cloned into plasmid pcDNA3.1 (Invitrogen). The resulting clones were designated pcDNA-622 and pcDNA-603. In this connection, the plasmid pcDNA3.1 contains a cytomegalovirus promoter sequence and may be used for expressing a novel potassium-dependent sodium-calcium exchanger in an animal cell.

The base sequences of the clones pcDNA-622 and pcDNA-603 were analyzed using a DNA sequencer (ABI377 DNA Sequencer; Applied Biosystems) by a dideoxy terminator method to obtain the base sequences of SEQ ID NOS: 1 and 3, respectively.

The base sequence of SEQ ID NO: 1 (total base pairs=1902 bp) contains an open reading frame represented by the sequence consisting of the 14th to 1882nd bases. The amino acid sequence deduced from the open reading frame and consisting of 622 amino acid residues was that of SEQ ID NO: 2.

The base sequence of SEQ ID NO: 3 (total base pairs=1845 bp) contains an open reading frame represented by the sequence consisting of the 14th to 1825th bases. The amino acid sequence deduced from the open reading frame and consisting of 603 amino acid residues was that of SEQ ID NO: 4.

Example 2

Analysis of Expression Distribution of Potassium-Dependent Sodium-Calcium Exchangers in Human Tissues An expression distribution of the gene (SEQ ID NO: 1) encoding the novel potassium-dependent sodium-calcium in human tissues was analyzed by a reverse transcriptase-polymerase chain reaction (RT-PCR) method in accordance with the following procedure.

Poly $A^+$ RNA (5 ng, respectively; Clontech) from each human tissue was treated with DNase, and then a first-strand cDNA was synthesized by carrying out a reverse transcription using an RT-PCR kit (SUPERSCRIPT First-Strand Synthesis System for RT-PCR; GIBCO-BRL).

A PCR was carried out using the resulting first-strand cDNA as a template, an oligonucleotide consisting of the base sequence of SEQ ID NO: 7 as a forward primer, an oligonucleotide consisting of the base sequence of SEQ ID NO: 8 as a reverse primer, and DNA Polymerase (PLATINUM Taq DNA Polymerase High-Fidelity; GIBCO-BRL). In the PCR, a thermal denaturation was first performed at 94° C. for 1 minute, and then a cycle consisting of reactions at 98° C. for 10 seconds, at 64° C. for 20 seconds, and at 68° C. for 1 minute and 30 seconds was repeated 35 times. In this connection, the base sequences of the primers are specific sequences commonly contained in both genes encoding the polypeptides consisting of the amino acid sequences of SEQ ID NOS: 2 and 4.

When the RT-PCR analysis of human peripheral leukocytes was carried out, DNA fragments of approximately 750 bp and approximately 700 bp were amplified. The DNA fragments of approximately 750 bp and approximately 700 bp contained "the sequence consisting of the 348th to 1101st bases in the base sequence of SEQ ID NO: 1" and "the sequence consisting of the 348th to 1044th bases in the base sequence of SEQ ID NO: 3", respectively. From the result, it was found that the mRNA of each potassium-dependent sodium-calcium exchanger of the present invention was expressed in human peripheral leukocytes.

Example 3

Expression of Potassium-Dependent Sodium-Calcium Exchangers in Animal Cells HEK293, Dede, and CHO Each polypeptide consisting of the amino acid sequence of SEQ ID NO: 2 or 4 was expressed in animal cells to detect a novel potassium-dependent sodium-calcium exchange activity of the polypeptide. As the animal cells, an HEK293 cell (ATCC: CRL-1573), a Dede cell (ATCC: CCL-39), and a CHO-dhfr⁻ cell (ATCC: CRL-9096) were used. HEK293 cells, Dede cells, or CHO-dhfr⁻ cells were transfected with the expression vector pcDNA-622 or pcDNA-603 prepared in Example 1 and a commercially available transfection reagent (LipofectAMINE2000; GIBCO-BRL) to express each potassium-dependent sodium-calcium exchanger in each cell. In this connection, the concrete procedure was carried out in accordance with a manual attached to the transfection reagent. Further, a cell transfected with the plasmid pcDNA3.1 was prepared as a control cell in a similar fashion. The resulting transfected cells were used in the following Examples 4 and 5.

Example 4

Detection of Potassium-Dependent Sodium-Calcium Exchange Activity

The sodium-calcium exchange activity was measured using each of the cells prepared in Example 3.

Sodium was incorporated into cells by changing the medium to an extracellular solution containing monensin [i.e., a solution containing 0.01 mmol/L monensin, 1 mmol/L ouabain, 146 mmol/L NaCl, 4 mmol/L KCl, 0.1 mmol/L CaCl$_2$, 2 mmol/L MgCl$_2$, 10 mmol/L glucose, 0.1% bovine serum albumin, and 10 mmol/L HEPES-Tris (pH=7.4)] and incubating the cells at 37° C. for 30 minutes. The solution was changed to an extracellular solution containing calcium chloride ($^{45}$CaCl$_2$; 55.5 kBq/mL) [i.e., a solution containing 0.01 mmol/L verapamil, 1 mmol/L ouabain, 150 mmol/L NaCl, 0.1 mmol/L CaCl$_2$, 2 mmol/L MgCl$_2$, 10 mmol/L glucose, 0.1% bovine serum albumin, and 10 mmol/L HEPES-Tris (pH=7.4); extracellular solution A], and the cells were allowed to stand at room temperature for 15 minutes to exchange the intracellular sodium ions for the calcium ions.

In addition, an extracellular solution in which choline chloride was substituted for NaCl (extracellular solution B) was used. Further, to examine the dependency on a potassium ion, an extracellular solution containing calcium chloride ($^{45}$CaCl$_2$; 55.5 kBq/mL) and potassium chloride [i.e., a solution containing 0.01 mmol/L verapamil, 1 mmol/L ouabain, 4 mmol/L KCl, 146 mmol/L choline chloride, 0.1 mmol/L CaCl$_2$, 2 mmol/L MgCl$_2$, 10 mmol/L glucose, 0.1% bovine serum albumin, and 10 mmol/L HEPES-Tris (pH=7.4); extracellular solution C] and an extracellular solution having a composition the same as that of extracellular solution C except that KCl was 150 mmol/L and that choline chloride was not contained (extracellular solution D) were used.

The treated cells were washed with a washing solution containing 120 mmol/L choline chloride, 10 mmol/L LaCl$_3$, and 10 mmol/L HEPES-Tris (pH=7.4) to remove calcium ions not incorporated, and then an intracellular calcium ion radioactivity was measured and analyzed by a liquid scintillation counter. In the HEK293 cells, Dede cells, or CHO-dhfr⁻ cells expressing the polypeptide consisting of the amino acid sequence of SEQ ID NO: 2 or 4, a higher radioactivity of approximately two times that obtained in the case of the extracellular solution A was measured when using the extracellular solution B (extracellular solution in which sodium was replaced with choline). Further, higher radioactivities of approximately five times and approximately ten times that obtained in the case of the extracellular solution A were measured when using the extracellular solutions C and D (extracellular solution containing potassium), respectively.

As described above, it was confirmed that, in the cells expressing the polypeptide consisting of the amino acid sequence of SEQ ID NO: 2 or 4 of the present invention, intracellular sodium ions can be exchanged for extracellular calcium ions more effectively in the presence of potassium ions, and that the polypeptide of the present invention consisting of the amino acid sequence of SEQ ID NO: 2 or 4 exhibits a potassium-dependent sodium-calcium exchange activity.

Example 5

Construction of Cell Strain Stably Expressing Novel Potassium-Dependent Sodium-Calcium Exchanger To construct a stable-expression cell strain, the Dede cells prepared in Example 3 were repetitively subcultured in a DMEM medium containing G-418 (GIBCO-BRL) at a final concentration of 400 mg/L, and the cells were seeded into wells of 96-well plates (5000 cells/well). The potassium-dependent sodium-calcium exchange activity in each well was measured in accordance with the method described in Example 4, to select cells having a potassium-dependent sodium-calcium exchange activity in which a radioactivity in the case of the extracellular solution C or D was 5000 cpm/well or more and an S/N ratio was 10 or more. The resulting stable-expression cell strains derived from a Dede cell were used in the following Example 6.

Example 6

Screening Substances Inhibiting Novel Potassium-Dependent Sodium-Calcium Exchange Activity Utilizing Radioisotope Calcium ($^{45}$Ca) Ion Release In accordance with the method described in Example 4, substances which inhibit an activity of the novel potassium-dependent sodium-calcium exchanger consisting of the amino acid sequence of SEQ ID NO: 2 or 4 were screened by measuring a calcium ion radioactivity.

The stable-expression cells derived from a Dede cell, prepared in Example 5, were seeded into each well of 96-well plates (5000 cells/well), and an inhibitory activity was determined by measuring a calcium ion radioactivity in accordance with the method described in Example 4, to screen substances which inhibit an activity of the novel potassium-dependent sodium-calcium exchanger consisting of the amino acid sequence of SEQ ID NO: 2 or 4. After cells were treated with monensin, each solution containing a test compound [i.e., a solution of a test compound dissolved in dimethyl sulfoxide (DMSO)] was added to the extracellular C or D containing calcium chloride ($^{45}$CaCl$_2$; 55.5 kBq/mL), and measured to select substances exhibiting an inhibitory activity of 30% or more.

As a result, two compounds which exhibited an activity of the novel potassium-dependent sodium-calcium exchanger consisting of the amino acid sequence of SEQ ID NO: 2 or 4, i.e., 2-[2-[4-(4-nitrobenzyloxy)phenyl]ethyl] isothiourea methanesulfonate [compound A; Japanese Unexamined Patent Publication (Kokai) 9-67336 or J Biol Chem. 1996. 271(37): 22391-7.] and 3',4'-dichlorobenzamil [compound B; catalog compound No. B-710, NIMH Chemical Inventory, U.S.A or Proc Natl Acad Sci U S A. 1984 May; 81(10): 3238-42.], were obtained.

Example 7

Effect of Inhibitors in Human Peripheral Polymorphonuclear Leukocytes

The compounds obtained in Example 6 were evaluated using human peripheral polymorphonuclear leukocytes (PMNs). A blood sample was obtained by collecting blood from a healthy adult. A ficoll solution for separation (monopoly resolving medium; Dainippon Pharmaceutical) was poured into each centrifuge tube, and a fresh blood component was laid on the ficoll solution. Centrifugation was carried out at 400×g at room temperature for 30 minutes to separate the upper layer (monocytes), the intermediate layer (PMNs), and the precipitate (erythrocytes). Each layer was collected in such a way that they were not mixed with each other, suspended in a phosphate buffered saline (PBS), and recentrifuged. Each collected layer was suspended in an RPMI1640 medium containing 0.2% bovine serum albumin (BSA), and used in the following experiment after counting the number of cells. A portion of the resulting PMN component was stained by a hematoxylin and eosin stain to confirm that neutrophils (approximately 95%) and eosinophils (approximately 5%) were contained.

A migration test was carried out using a 24-well disposable chemotaxis chamber Transwell 3 μm; Corning). Each test solution in which compound A or B (final concentration=10 μmol/L, 30 μmol/L, and 100 μmol/L) were contained in a medium (0.2% BSA, RPMI1640 medium) containing 100 nmol/L formylmethionyl-leucinyl-phenylalanine (fMLP) was prepared, and 1 mL of each test solution was added to each of the lower wells. The collected PMNs were added to each of the upper wells ($2.0 \times 10^6$ cells/well; 0.2 mL) and incubated at 37° C. for 1 hour. The numbers of cells which migrated to the lower wells were counted by a hemacytometer. The test was independently repeated three times.

The results are shown in Table 1. Each value shown in Table 1 is a relative value when the value obtained in the case of using DMSO instead of the test compounds is regarded as 100. Further, each value shown in Table 1 is an average and a standard deviation (SD) on the basis of three independent experiments. Data obtained in the case that PMNs were not stimulated by fMLP (BG) are shown in Table 1.

As shown in Table 1, compounds A and B inhibited the migration of PMNs dose-dependently. From the results, it was found that compounds which inhibit an activity of the novel potassium-dependent sodium-calcium exchanger consisting of the amino acid sequence of SEQ ID NO: 2 or 4 have an effect capable of inhibiting the migration of PMNs. That is, it was found that such compounds have an advantageous effect as a therapeutic agent for cell injury due to postischemic reperfusion and/or an inflammatory disease.

TABLE 1

|  |  | Number of migrating cells (relative value) |
| --- | --- | --- |
| Control | DMSO | 100 |
| compound A | 10 μmol/L | 78.18 ± 25.93 |
|  | 30 μmol/L | 29.50 ± 26.16 |
|  | 100 μmol/L | 16.84 ± 10.78 |
| compound B | 10 μmol/L | 100.68 ± 7.27 |
|  | 30 μmol/L | 72.90 ± 15.85 |
|  | 100 μmol/L | 44.58 ± 32.82 |
| BG | fMLP (−) | 19.22 ± 6.20 |

INDUSTRIAL APPLICABILITY

The polypeptide of the present invention is a potassium-dependent sodium-calcium exchanger expressed in peripheral leukocytes, and thus is involved in leukocyte activation, cell injury due to postischemic reperfusion, and inflammation. Therefore, a substance which inhibits the polypeptide of the present invention is useful in inhibiting leukocyte activation and treating cell injury due to postischemic reperfusion and/or an inflammatory disease.

Further, the polypeptide of the present invention and the cell of the present invention expressing the polypeptide at the surface thereof are useful in screening an inhibitor of leukocyte activation and a therapeutic agent for cell injury due to postischemic reperfusion and/or an inflammatory disease. A convenient screening system for obtaining an inhibitor of leukocyte activation and a therapeutic agent for cell injury due to postischemic reperfusion and/or an inflammatory disease can be provided by using the cell of the present invention. Furthermore, the polynucleotide and the expression vector of the present invention is useful in manufacturing a screening tool for an inhibitor of leukocyte activation and a therapeutic agent for cell injury and/or an inflammatory disease.

According to the screening tool or screening method of the present invention, a substance useful as an inhibitor of leukocyte activation and a therapeutic agent for cell injury due to postischemic reperfusion and an inflammatory disease can be screened. The pharmaceutical composition of the present invention for inhibiting leukocyte activation is useful in preventing cell injury due to postischemic reperfusion and in treating and/or preventing an inflammatory disease.

FREE TEXT IN SEQUENCE LISTING

Features of "Artificial Sequence" are described in the numeric identifier <223> in the Sequence Listing. More particularly, each of the base sequences of SEQ ID NOS: 5 to 8 is an artificially synthesized primer sequence.

Although the present invention has been described with reference to specific embodiments, various changes and modifications obvious to those skilled in the art are possible without departing from the scope of the appended claims. calcium axchange activity in the polypeptide is inhibited, and (3) selecting a substance which inhibits the potassium-dependent sodium-calcium exchange activity in the polypeptide.

9. A method for screening an inhibitor of leukocyte activation, comprising the steps of:
(1) bringing a cell expressing the polypeptide according to and one of claims 1 to 3 into contact with a substance to be tested,
(2) analyzing whether or not a potassium-dependent sodium-calcium exchange activity in the polypeptide is inhibited, and
(3) selecting a substance which inhibits the potassium-dependent sodium-calcium exchange activity in the polypeptide.

10. A method for screening a therapeutic agent for postischemic reperfusion injury and/or an inflammatory disease, comprising the steps of:
(1) bringing a cell expressing the polypeptide according to any one of claims 1 to 3 into contact with a substance to be tested,
(2) analyzing whether or not a potassium-dependent sodium-calcium exchange activity in the polypeptide is inhibited, and
(3) selecting a substance which inhibits the potassium-dependent sodium-calcium exchange activity in the polypeptide.

11. A process for manufacturing a pharmaceutical composition for theating postischemic reperfusion injury and/or an inflammatory disease, comprising the steps of:
(1) bringing a cell expressing the polypeptide according to any one of claims 1 to 3 into contact with a substance to be tested,

---

The invention claimed is:

1. An isolated polypeptide (a) consisting of the amino acid sequence of SEQ ID NO: 2, or (b) exhibiting a potassium-dependent sodium-calcium exchange activity and consisting of an amino acid sequence in which 1 to 5 amino acids in total are substituted, deleted, inserted, and/or added at one or plural portions in the amino acid sequence of SEQ ID NO: 2.

2. The isolated polypeptide according to claim 1, wherein the sodium-calcium exchange activity is a reverse sodium-calcium exchange activity.

3. An isolated polynucleotide encoding the polypeptide according to claim 1 or 2.

4. An expression vector comprising the polynucleotide according to claim 3.

5. A cell transfected with the expression vector according to claim 4.

6. A method for producing the isolated polypeptide according to claim 1 or 2, the method comprising expressing a polynucleotide encoding the polypeptide in a cell transfected with an expression vector comprising the polynucleotide.

7. A method for screening for an inhibitor of the polypeptide according to claim 1 or 2, comprising the steps of:
    (a) introducing into a cell an isolated polynucleotide encoding the polypeptide of claim 1 or 2,
    (b) bringing the cell expressing the polypeptide into contact with a substance to be tested,
    (c) analyzing whether or not a potassium-dependent sodium-calcium exchange activity in the polypeptide is inhibited, and
    (d) selecting the substance that inhibits the potassium-dependent sodium-calcium exchange activity in the polypeptide.

8. A method for screening for an inhibitor of leukocyte activation, comprising the steps of:
    (a) introducing into a cell an isolated polynucleotide encoding a polypeptide
        (i) consisting of the amino acid sequence of SEQ ID NO: 2, or
        (ii) exhibiting a potassium-dependent sodium-calcium exchange activity and consisting of an amino acid sequence in which 1 to 5 amino acids in total are substituted, deleted, inserted, and/or added at one or plural portions in the amino acid sequence of SEQ ID NO: 2,
    (b) bringing the cell expressing the polypeptide into contact with a substance to be tested,
    (c) analyzing whether or not a potassium-dependent sodium-calcium exchange activity in the polypeptide is inhibited,
    (d) selecting the substance that inhibits the potassium-dependent sodium-calcium exchange activity in the polypeptide, and
    (e) confirming that the selected substance inhibits leukocyte activation.

9. A method for screening for a therapeutic agent for postischemic reperfusion injury and/or an inflammatory disease, comprising the steps of:
    (a) introducing into a cell an isolated polynucleotide encoding a polypeptide
        (i) consisting of the amino acid sequence of SEQ ID NO: 2, or
        (ii) exhibiting a potassium-dependent sodium-calcium exchange activity and consisting of an amino acid sequence in which 1 to 5 amino acids in total are substituted, deleted, inserted, and/or added at one or plural portions in the amino acid sequence of SEQ ID NO: 2,
    (b) bringing the cell expressing the polypeptide into contact with a substance to be tested, (c) analyzing whether or not a potassium-dependent sodium-calcium exchange activity in the polypeptide is inhibited, and (d) selecting the substance that inhibits the potassium-dependent sodium-calcium exchange activity in the polypeptide for use as a therapeutic agent for postischemic reperfusion injury and/or an inflammatory disease.

10. A process for manufacturing a pharmaceutical composition for treating postischemic reperfusion injury and/or an inflammatory disease, comprising the steps of:

(a) introducing into a cell an isolated polynucleotide encoding a polypeptide
  (i) consisting of the amino acid sequence of SEQ ID NO: 2, or
  (ii) exhibiting a potassium-dependent sodium-calcium exchange activity and consisting of an amino acid sequence in which 1 to 5 amino acids in total are substituted, deleted, inserted, and/or added at one or plural portions in the amino acid sequence of SEQ ID NO: 2, (b) bringing the cell expressing the polypeptide into contact with a substance to be tested, (c) analyzing whether or not a potassium-dependent sodium-calcium exchange activity in the polypeptide is inhibited, (d) selecting the substance that inhibits the potassium-dependent sodium-calcium exchange activity in the polypeptide, and (e) preparing a pharmaceutical composition containing the substance.

\* \* \* \* \*

SEQUENCE LISTING

<160> NUMBER OF SEQ ID NOS: 8

<210> SEQ ID NO 1
<211> LENGTH: 1902
<212> TYPE: DNA
<213> ORGANISM: Homo sapiens
<220> FEATURE:
<221> NAME/KEY: CDS
<222> LOCATION: (14)..(1882)
<223> OTHER INFORMATION:
<220> FEATURE:
<223> OTHER INFORMATION: Inventor: Nozawa, Katsura; Mochizuki, Shinobu

<400> SEQUENCE: 1

```
gggaattcga tcc atg gcg ctc cgc ggg acc ctc cgg ccg ctc aaa gtt            49
            Met Ala Leu Arg Gly Thr Leu Arg Pro Leu Lys Val
            1               5                   10 cgc agg agg cga gag atg ctg ccg cag caa gtc ggc ttc gtg tgc gcg          97
Arg Arg Arg Arg Glu Met Leu Pro Gln Gln Val Gly Phe Val Cys Ala
                15                  20                  25 gtg ctg gcc ctg gtg tgc tgt gcg tcc ggc ctc ttc ggc agc ttg ggg          145
Val Leu Ala Leu Val Cys Cys Ala Ser Gly Leu Phe Gly Ser Leu Gly
        30                  35                  40 cac aaa aca gct tct gct agc aaa cgt gtc ctg cca gac aca tgg aga          193
His Lys Thr Ala Ser Ala Ser Lys Arg Val Leu Pro Asp Thr Trp Arg
45                  50                  55                  60 aat aga aag ttg atg gcc cca gtg aat ggg aca cag aca gcc aag aac          241
Asn Arg Lys Leu Met Ala Pro Val Asn Gly Thr Gln Thr Ala Lys Asn
                65                  70                  75 tgc aca gat cct gcg att cac gag ttc ccc aca gat ctg ttc tcc aat          289
Cys Thr Asp Pro Ala Ile His Glu Phe Pro Thr Asp Leu Phe Ser Asn
            80                  85                  90 aag gag cga cag cac gga gcc gtc ctg ctg cac atc ctt ggt gct ctg          337
Lys Glu Arg Gln His Gly Ala Val Leu Leu His Ile Leu Gly Ala Leu
        95                  100                 105 tat atg ttc tat gcc ttg gcc ata gtg tgc gat gac ttc ttt gtt ccg          385
Tyr Met Phe Tyr Ala Leu Ala Ile Val Cys Asp Asp Phe Phe Val Pro
    110                 115                 120 tct cta gag aag atc tgt gag aga ctc cat ctg agc gaa gat gtg gct          433
Ser Leu Glu Lys Ile Cys Glu Arg Leu His Leu Ser Glu Asp Val Ala
125                 130                 135                 140 gga gcc acc ttc atg gct gca gga agc tca acg cca gag ctg ttt gcg          481
Gly Ala Thr Phe Met Ala Ala Gly Ser Ser Thr Pro Glu Leu Phe Ala
                145                 150                 155 tct gtt att ggg gtg ttc atc acc cac ggg gac gtc ggg gtg ggc acc          529
```

|     |     |     |     |     |     |     |     |     |     |     |     |     |
|---|---|---|---|---|---|---|---|---|---|---|---|---|
| Ser | Val | Ile | Gly | Val | Phe | Ile | Thr | His | Gly | Asp | Val | Gly | Val | Gly | Thr |
|     |     | 160 |     |     |     |     | 165 |     |     |     | 170 |     |

```
atc gtg ggc tct gct gtg ttc aac atc ctg tgc ata att gga gtg tgc       577
Ile Val Gly Ser Ala Val Phe Asn Ile Leu Cys Ile Ile Gly Val Cys
        175                 180                 185 gga ctg ttt gct ggc cag gtg gtc cgt ctg acg tgg tgg gcc gtg tgc       625
Gly Leu Phe Ala Gly Gln Val Val Arg Leu Thr Trp Trp Ala Val Cys
190                 195                 200 cga gac tcc gtg tac tac acc atc tct gtc atc gtg ctc atc gtg ttc       673
Arg Asp Ser Val Tyr Tyr Thr Ile Ser Val Ile Val Leu Ile Val Phe
205                 210                 215                 220 ata tat gat gaa caa att gtg tgg tgg gaa ggc ctg gtg ctc atc atc       721
Ile Tyr Asp Glu Gln Ile Val Trp Trp Glu Gly Leu Val Leu Ile Ile
                225                 230                 235 ttg tat gtg ttt tat att ctg atc atg aag tac aat gtg aag atg caa       769
Leu Tyr Val Phe Tyr Ile Leu Ile Met Lys Tyr Asn Val Lys Met Gln
        240                 245                 250 gcc ttt ttc aca gtc aaa caa aag agc att gca aac ggt aac ccg gtc       817
Ala Phe Phe Thr Val Lys Gln Lys Ser Ile Ala Asn Gly Asn Pro Val
            255                 260                 265 aac agt gag ctg gag gct ggt aat gat ttc tat gac ggt agc tat gat       865
Asn Ser Glu Leu Glu Ala Gly Asn Asp Phe Tyr Asp Gly Ser Tyr Asp
        270                 275                 280 gac cct tcc gtg cca ttg ctg ggg caa gtg aag gag aag cca cag tat       913
Asp Pro Ser Val Pro Leu Leu Gly Gln Val Lys Glu Lys Pro Gln Tyr
285                 290                 295                 300 ggc aag aac ccc gtg gtg atg gtg gac gag att atg agc tcc agc cct       961
Gly Lys Asn Pro Val Val Met Val Asp Glu Ile Met Ser Ser Ser Pro
                305                 310                 315 ccc aag ttc acc ttc cct gaa gca ggc tta cga atc atg atc acc aat      1009
Pro Lys Phe Thr Phe Pro Glu Ala Gly Leu Arg Ile Met Ile Thr Asn
        320                 325                 330 aag ttt gga ccc agg acc cga cta cgg atg gcc agc agg atc atc att      1057
Lys Phe Gly Pro Arg Thr Arg Leu Arg Met Ala Ser Arg Ile Ile Ile
            335                 340                 345 aat gag cgg cag aga ctg atc aac tcg gcc aat ggt gtg agc agt aag      1105
Asn Glu Arg Gln Arg Leu Ile Asn Ser Ala Asn Gly Val Ser Ser Lys
350                 355                 360 ccg ctt caa aac ggg agg cac gag aac att gag aac ggg aat gtt cct      1153
Pro Leu Gln Asn Gly Arg His Glu Asn Ile Glu Asn Gly Asn Val Pro
365                 370                 375                 380 gtg gaa aac ccc gaa gac cct cag cag aat cag gag cag cag ccg ccg      1201
Val Glu Asn Pro Glu Asp Pro Gln Gln Asn Gln Glu Gln Gln Pro Pro
                385                 390                 395 cca cag cca cca ccg cca gag cca gag ccg gtg gag gct gac ttc ctg      1249
Pro Gln Pro Pro Pro Pro Glu Pro Glu Pro Val Glu Ala Asp Phe Leu
        400                 405                 410 tcc ccc ttc tcc gtg ccg gag gcc aga ggg gac aag gtc aag tgg gtg      1297
Ser Pro Phe Ser Val Pro Glu Ala Arg Gly Asp Lys Val Lys Trp Val
            415                 420                 425 ttc acc tgg ccc ctc atc ttc ctc ctg tgc gtc acc att ccc aac tgc      1345
Phe Thr Trp Pro Leu Ile Phe Leu Leu Cys Val Thr Ile Pro Asn Cys
430                 435                 440 agc aag ccc cgc tgg gag aag ttc ttc atg gtc acc ttc atc acc gcc      1393
Ser Lys Pro Arg Trp Glu Lys Phe Phe Met Val Thr Phe Ile Thr Ala
445                 450                 455                 460 acg ctg tgg atc gct gtg ttc tcc tac atc atg gtg tgg ctg gtg act      1441
Thr Leu Trp Ile Ala Val Phe Ser Tyr Ile Met Val Trp Leu Val Thr
                465                 470                 475
```

```
att atc gga tac aca ctt ggg atc ccg gat gtc atc atg ggc att act        1489
Ile Ile Gly Tyr Thr Leu Gly Ile Pro Asp Val Ile Met Gly Ile Thr
        480                 485                 490 ttc ctg gca gca ggg aca agt gtt cca gac tgc atg gcc agc cta att        1537
Phe Leu Ala Ala Gly Thr Ser Val Pro Asp Cys Met Ala Ser Leu Ile
            495                 500                 505 gtg gcg aga caa ggc ctt ggg gac atg gca gtc tcc aac acc ata gga        1585
Val Ala Arg Gln Gly Leu Gly Asp Met Ala Val Ser Asn Thr Ile Gly
510                 515                 520 agc aac gtg ttt gac atc ctg gta gga ctt ggt gta ccg tgg ggc ctg        1633
Ser Asn Val Phe Asp Ile Leu Val Gly Leu Gly Val Pro Trp Gly Leu
525                 530                 535                 540 cag acc atg gtt gtt aat tat gga tca aca gtg aag atc aac agc cgg        1681
Gln Thr Met Val Val Asn Tyr Gly Ser Thr Val Lys Ile Asn Ser Arg
                545                 550                 555 ggg ctg gtc tat tcc gtg gtc ctg ttg ctg ggc tct gtc gct ctc acc        1729
Gly Leu Val Tyr Ser Val Val Leu Leu Leu Gly Ser Val Ala Leu Thr
        560                 565                 570 gtc ctc ggc atc cac cta aac aag tgg cga ctg gac cgg aag ctg ggt        1777
Val Leu Gly Ile His Leu Asn Lys Trp Arg Leu Asp Arg Lys Leu Gly
            575                 580                 585 gtc tac gtg ctg gtt ctc tac gcc atc ttc ttg tgc ttc tcc ata atg        1825
Val Tyr Val Leu Val Leu Tyr Ala Ile Phe Leu Cys Phe Ser Ile Met
590                 595                 600 ata gag ttt aac gtc ttt acc ttc gtc aac ttg ccg atg tgc cgg gaa        1873
Ile Glu Phe Asn Val Phe Thr Phe Val Asn Leu Pro Met Cys Arg Glu
605                 610                 615                 620 gac gat tag cgctgagtcg cggtacctgg                                       1902
Asp Asp <210> SEQ ID NO 2
<211> LENGTH: 622
<212> TYPE: PRT
<213> ORGANISM: Homo sapiens

<400> SEQUENCE: 2

Met Ala Leu Arg Gly Thr Leu Arg Pro Leu Lys Val Arg Arg Arg
1               5                   10                  15

Glu Met Leu Pro Gln Gln Val Gly Phe Val Cys Ala Val Leu Ala Leu
            20                  25                  30

Val Cys Cys Ala Ser Gly Leu Phe Gly Ser Leu Gly His Lys Thr Ala
        35                  40                  45

Ser Ala Ser Lys Arg Val Leu Pro Asp Thr Trp Arg Asn Arg Lys Leu
    50                  55                  60

Met Ala Pro Val Asn Gly Thr Gln Thr Ala Lys Asn Cys Thr Asp Pro
65                  70                  75                  80

Ala Ile His Glu Phe Pro Thr Asp Leu Phe Ser Asn Lys Glu Arg Gln
                85                  90                  95

His Gly Ala Val Leu Leu His Ile Leu Gly Ala Leu Tyr Met Phe Tyr
            100                 105                 110

Ala Leu Ala Ile Val Cys Asp Asp Phe Phe Val Pro Ser Leu Glu Lys
        115                 120                 125

Ile Cys Glu Arg Leu His Leu Ser Glu Asp Val Ala Gly Ala Thr Phe
    130                 135                 140

Met Ala Ala Gly Ser Ser Thr Pro Glu Leu Phe Ala Ser Val Ile Gly
145                 150                 155                 160

Val Phe Ile Thr His Gly Asp Val Gly Val Gly Thr Ile Val Gly Ser
                165                 170                 175
```

-continued

```
Ala Val Phe Asn Ile Leu Cys Ile Ile Gly Val Cys Gly Leu Phe Ala
            180                 185                 190

Gly Gln Val Val Arg Leu Thr Trp Trp Ala Val Cys Arg Asp Ser Val
        195                 200                 205

Tyr Tyr Thr Ile Ser Val Ile Val Leu Ile Val Phe Ile Tyr Asp Glu
        210                 215                 220

Gln Ile Val Trp Trp Glu Gly Leu Val Leu Ile Ile Leu Tyr Val Phe
225                 230                 235                 240

Tyr Ile Leu Ile Met Lys Tyr Asn Val Lys Met Gln Ala Phe Phe Thr
            245                 250                 255

Val Lys Gln Lys Ser Ile Ala Asn Gly Asn Pro Val Asn Ser Glu Leu
        260                 265                 270

Glu Ala Gly Asn Asp Phe Tyr Asp Gly Ser Tyr Asp Asp Pro Ser Val
        275                 280                 285

Pro Leu Leu Gly Gln Val Lys Glu Lys Pro Gln Tyr Gly Lys Asn Pro
        290                 295                 300

Val Val Met Val Asp Glu Ile Met Ser Ser Pro Pro Lys Phe Thr
305                 310                 315                 320

Phe Pro Glu Ala Gly Leu Arg Ile Met Ile Thr Asn Lys Phe Gly Pro
                325                 330                 335

Arg Thr Arg Leu Arg Met Ala Ser Arg Ile Ile Ile Asn Glu Arg Gln
            340                 345                 350

Arg Leu Ile Asn Ser Ala Asn Gly Val Ser Ser Lys Pro Leu Gln Asn
        355                 360                 365

Gly Arg His Glu Asn Ile Glu Asn Gly Asn Val Pro Val Glu Asn Pro
        370                 375                 380

Glu Asp Pro Gln Gln Asn Gln Glu Gln Gln Pro Pro Gln Pro Pro
385                 390                 395                 400

Pro Pro Glu Pro Glu Pro Val Glu Ala Asp Phe Leu Ser Pro Phe Ser
                405                 410                 415

Val Pro Glu Ala Arg Gly Asp Lys Val Lys Trp Val Phe Thr Trp Pro
            420                 425                 430

Leu Ile Phe Leu Leu Cys Val Thr Ile Pro Asn Cys Ser Lys Pro Arg
        435                 440                 445

Trp Glu Lys Phe Phe Met Val Thr Phe Ile Thr Ala Thr Leu Trp Ile
        450                 455                 460

Ala Val Phe Ser Tyr Ile Met Val Trp Leu Val Thr Ile Ile Gly Tyr
465                 470                 475                 480

Thr Leu Gly Ile Pro Asp Val Ile Met Gly Ile Thr Phe Leu Ala Ala
            485                 490                 495

Gly Thr Ser Val Pro Asp Cys Met Ala Ser Leu Ile Val Ala Arg Gln
        500                 505                 510

Gly Leu Gly Asp Met Ala Val Ser Asn Thr Ile Gly Ser Asn Val Phe
        515                 520                 525

Asp Ile Leu Val Gly Leu Gly Val Pro Trp Gly Leu Gln Thr Met Val
        530                 535                 540

Val Asn Tyr Gly Ser Thr Val Lys Ile Asn Ser Arg Gly Leu Val Tyr
545                 550                 555                 560

Ser Val Val Leu Leu Gly Ser Val Ala Leu Thr Val Leu Gly Ile
            565                 570                 575

His Leu Asn Lys Trp Arg Leu Asp Arg Lys Leu Gly Val Tyr Val Leu
        580                 585                 590
```

```
Val Tyr Ala Ile Phe Leu Cys Phe Ser Ile Met Ile Glu Phe Asn
            595                 600                 605

Val Phe Thr Phe Val Asn Leu Pro Met Cys Arg Glu Asp Asp
    610                 615                 620

<210> SEQ ID NO 3
<211> LENGTH: 1845
<212> TYPE: DNA
<213> ORGANISM: Homo sapiens
<220> FEATURE:
<221> NAME/KEY: CDS
<222> LOCATION: (14)..(1825)
<223> OTHER INFORMATION:

<400> SEQUENCE: 3
caggaattcc acc atg gcg ctc cgc ggg acc ctc cgg ccg ctc aaa gtt          49
            Met Ala Leu Arg Gly Thr Leu Arg Pro Leu Lys Val
             1               5                  10 cgc agg agg cga gag atg ctg ccg cag caa gtc ggc ttc gtg tgc gcg         97
Arg Arg Arg Arg Glu Met Leu Pro Gln Gln Val Gly Phe Val Cys Ala
         15                  20                  25 gtg ctg gcc ctg gtg tgc tgt gcg tcc ggc ctc ttc ggc agc ttg ggg        145
Val Leu Ala Leu Val Cys Cys Ala Ser Gly Leu Phe Gly Ser Leu Gly
     30                  35                  40 cac aaa aca gct tct gct agc aaa cgt gtc ctg cca gac aca tgg aga        193
His Lys Thr Ala Ser Ala Ser Lys Arg Val Leu Pro Asp Thr Trp Arg
45                  50                  55                  60 aat aga aag ttg atg gcc cca gtg aat ggg aca cag aca gcc aag aac        241
Asn Arg Lys Leu Met Ala Pro Val Asn Gly Thr Gln Thr Ala Lys Asn
             65                  70                  75 tgc aca gat cct gcg att cac gag ttc ccc aca gat ctg ttc tcc aat        289
Cys Thr Asp Pro Ala Ile His Glu Phe Pro Thr Asp Leu Phe Ser Asn
         80                  85                  90 aag gag cga cag cac gga gcc gtc ctg ctg cac atc ctt ggt gct ctg        337
Lys Glu Arg Gln His Gly Ala Val Leu Leu His Ile Leu Gly Ala Leu
     95                 100                 105 tat atg ttc tat gcc ttg gcc ata gtg tgc gat gac ttc ttt gtt ccg        385
Tyr Met Phe Tyr Ala Leu Ala Ile Val Cys Asp Asp Phe Phe Val Pro
110                 115                 120 tct cta gag aag atc tgt gag aga ctc cat ctg agc gaa gat gtg gct        433
Ser Leu Glu Lys Ile Cys Glu Arg Leu His Leu Ser Glu Asp Val Ala
125                 130                 135                 140 gga gcc acc ttc atg gct gca gga agc tca acg cca gag ctg ttt gcg        481
Gly Ala Thr Phe Met Ala Ala Gly Ser Ser Thr Pro Glu Leu Phe Ala
                145                 150                 155 tct gtt att ggg gtg ttc atc acc cac ggg gac gtc ggg gtg ggc acc        529
Ser Val Ile Gly Val Phe Ile Thr His Gly Asp Val Gly Val Gly Thr
         160                 165                 170 atc gtg ggc tct gct gtg ttc aac atc ctg tgc ata att gga gtg tgc        577
Ile Val Gly Ser Ala Val Phe Asn Ile Leu Cys Ile Ile Gly Val Cys
     175                 180                 185 gga ctg ttt gct ggc cag gtg gtc cgt ctg acg tgg tgg gcc gtg tgc        625
Gly Leu Phe Ala Gly Gln Val Val Arg Leu Thr Trp Trp Ala Val Cys
190                 195                 200 cga gac tcc gtg tac tac acc atc tct gtc atc gtg ctc atc gtg ttc        673
Arg Asp Ser Val Tyr Tyr Thr Ile Ser Val Ile Val Leu Ile Val Phe
205                 210                 215                 220 ata tat gat gaa caa att gtg tgg tgg gaa ggc ctg gtg ctc atc atc        721
Ile Tyr Asp Glu Gln Ile Val Trp Trp Glu Gly Leu Val Leu Ile Ile
                225                 230                 235 ttg tat gtg ttt tat att ctg atc atg aag tac aat gtg aag atg caa        769
```

```
                                                        -continued

Leu Tyr Val Phe Tyr Ile Leu Ile Met Lys Tyr Asn Val Lys Met Gln
            240                 245                 250 gcc ttt ttc aca gtc aaa caa aag agc att gca aac ggt aac ccg gtc        817
Ala Phe Phe Thr Val Lys Gln Lys Ser Ile Ala Asn Gly Asn Pro Val
        255                 260                 265 aac agt gag ctg gag gct gtg aag gag aag cca cag tat ggc aag aac        865
Asn Ser Glu Leu Glu Ala Val Lys Glu Lys Pro Gln Tyr Gly Lys Asn
270                 275                 280 ccc gtg gtg atg gtg gac gag att atg agc tcc agc cct ccc aag ttc        913
Pro Val Val Met Val Asp Glu Ile Met Ser Ser Ser Pro Pro Lys Phe
285                 290                 295                 300 acc ttc cct gaa gca ggc tta cga atc atg atc acc aat aag ttt gga        961
Thr Phe Pro Glu Ala Gly Leu Arg Ile Met Ile Thr Asn Lys Phe Gly
                305                 310                 315 ccc agg acc cga cta cgg atg gcc agc agg atc atc att aat gag cgg       1009
Pro Arg Thr Arg Leu Arg Met Ala Ser Arg Ile Ile Ile Asn Glu Arg
            320                 325                 330 cag aga ctg atc aac tcg gcc aat ggt gtg agc agt aag ccg ctt caa       1057
Gln Arg Leu Ile Asn Ser Ala Asn Gly Val Ser Ser Lys Pro Leu Gln
        335                 340                 345 aac ggg agg cac gag aac att gag aac ggg aat gtt cct gtg gaa aac       1105
Asn Gly Arg His Glu Asn Ile Glu Asn Gly Asn Val Pro Val Glu Asn
350                 355                 360 ccc gaa gac cct cag cag aat cag gag cag cag ccg ccg cca cag cca       1153
Pro Glu Asp Pro Gln Gln Asn Gln Glu Gln Gln Pro Pro Pro Gln Pro
365                 370                 375                 380 cca ccg cca gag cca gag ccg gtg gag gct gac ttc ctg tcc ccc ttc       1201
Pro Pro Pro Glu Pro Glu Pro Val Glu Ala Asp Phe Leu Ser Pro Phe
                385                 390                 395 tcc gtg ccg gag gcc aga ggg gac aag gtc aag tgg gtg ttc acc tgg       1249
Ser Val Pro Glu Ala Arg Gly Asp Lys Val Lys Trp Val Phe Thr Trp
            400                 405                 410 ccc ctc atc ttc ctc ctg tgc gtc acc att ccc aac tgc agc aag ccc       1297
Pro Leu Ile Phe Leu Leu Cys Val Thr Ile Pro Asn Cys Ser Lys Pro
        415                 420                 425 cgc tgg gag aag ttc ttc atg gtc acc ttc atc acc gcc acg ctg tgg       1345
Arg Trp Glu Lys Phe Phe Met Val Thr Phe Ile Thr Ala Thr Leu Trp
430                 435                 440 atc gct gtg ttc tcc tac atc atg gtg tgg ctg gtg act att atc gga       1393
Ile Ala Val Phe Ser Tyr Ile Met Val Trp Leu Val Thr Ile Ile Gly
445                 450                 455                 460 tac aca ctt ggg atc ccg gat gtc atc atg ggc att act ttc ctg gca       1441
Tyr Thr Leu Gly Ile Pro Asp Val Ile Met Gly Ile Thr Phe Leu Ala
                465                 470                 475 gca ggg aca agt gtt cca gac tgc atg gcc agc cta att gtg gcg aga       1489
Ala Gly Thr Ser Val Pro Asp Cys Met Ala Ser Leu Ile Val Ala Arg
            480                 485                 490 caa ggc ctt ggg gac atg gca gtc tcc aac acc ata gga agc aac gtg       1537
Gln Gly Leu Gly Asp Met Ala Val Ser Asn Thr Ile Gly Ser Asn Val
        495                 500                 505 ttt gac atc ctg gta gga ctt ggt gta ccg tgg ggc ctg cag acc atg       1585
Phe Asp Ile Leu Val Gly Leu Gly Val Pro Trp Gly Leu Gln Thr Met
510                 515                 520 gtt gtt aat tat gga tca aca gtg aag atc aac agc cgg ggg ctg gtc       1633
Val Val Asn Tyr Gly Ser Thr Val Lys Ile Asn Ser Arg Gly Leu Val
525                 530                 535                 540 tat tcc gtg gtc ctg ttg ctg ggc tct gtc gct ctc acc gtc ctc ggc       1681
Tyr Ser Val Val Leu Leu Leu Gly Ser Val Ala Leu Thr Val Leu Gly
                545                 550                 555
```

-continued

```
atc cac cta aac aag tgg cga ctg gac cgg aag ctg ggt gtc tac gtg    1729
Ile His Leu Asn Lys Trp Arg Leu Asp Arg Lys Leu Gly Val Tyr Val
        560                 565                 570 ctg gtt ctc tac gcc atc ttc ttg tgc ttc tcc ata atg ata gag ttt    1777
Leu Val Leu Tyr Ala Ile Phe Leu Cys Phe Ser Ile Met Ile Glu Phe
    575                 580                 585 aac gtc ttt acc ttc gtc aac ttg ccg atg tgc cgg gaa gac gat tag    1825
Asn Val Phe Thr Phe Val Asn Leu Pro Met Cys Arg Glu Asp Asp
590                 595                 600 cgctgagtcg cggtacctgg                                              1845
```

<210> SEQ ID NO 4
<211> LENGTH: 603
<212> TYPE: PRT
<213> ORGANISM: Homo sapiens

<400> SEQUENCE: 4

```
Met Ala Leu Arg Gly Thr Leu Arg Pro Leu Lys Val Arg Arg Arg Arg
1               5                   10                  15

Glu Met Leu Pro Gln Gln Val Gly Phe Val Cys Ala Val Leu Ala Leu
            20                  25                  30

Val Cys Cys Ala Ser Gly Leu Phe Gly Ser Leu Gly His Lys Thr Ala
        35                  40                  45

Ser Ala Ser Lys Arg Val Leu Pro Asp Thr Trp Arg Asn Arg Lys Leu
    50                  55                  60

Met Ala Pro Val Asn Gly Thr Gln Thr Ala Lys Asn Cys Thr Asp Pro
65                  70                  75                  80

Ala Ile His Glu Phe Pro Thr Asp Leu Phe Ser Asn Lys Glu Arg Gln
                85                  90                  95

His Gly Ala Val Leu Leu His Ile Leu Gly Ala Leu Tyr Met Phe Tyr
            100                 105                 110

Ala Leu Ala Ile Val Cys Asp Asp Phe Phe Val Pro Ser Leu Glu Lys
        115                 120                 125

Ile Cys Glu Arg Leu His Leu Ser Glu Asp Val Ala Gly Ala Thr Phe
    130                 135                 140

Met Ala Ala Gly Ser Ser Thr Pro Glu Leu Phe Ala Ser Val Ile Gly
145                 150                 155                 160

Val Phe Ile Thr His Gly Asp Val Gly Val Gly Thr Ile Val Gly Ser
                165                 170                 175

Ala Val Phe Asn Ile Leu Cys Ile Ile Gly Val Cys Gly Leu Phe Ala
            180                 185                 190

Gly Gln Val Val Arg Leu Thr Trp Trp Ala Val Cys Arg Asp Ser Val
        195                 200                 205

Tyr Tyr Thr Ile Ser Val Ile Val Leu Ile Val Phe Ile Tyr Asp Glu
    210                 215                 220

Gln Ile Val Trp Trp Glu Gly Leu Val Leu Ile Leu Tyr Val Phe
225                 230                 235                 240

Tyr Ile Leu Ile Met Lys Tyr Asn Val Lys Met Gln Ala Phe Phe Thr
                245                 250                 255

Val Lys Gln Lys Ser Ile Ala Asn Gly Asn Pro Val Asn Ser Glu Leu
            260                 265                 270

Glu Ala Val Lys Glu Lys Pro Gln Tyr Gly Lys Asn Pro Val Val Met
        275                 280                 285

Val Asp Glu Ile Met Ser Ser Ser Pro Pro Lys Phe Thr Phe Pro Glu
    290                 295                 300
```

```
Ala Gly Leu Arg Ile Met Ile Thr Asn Lys Phe Gly Pro Arg Thr Arg
305                 310                 315                 320

Leu Arg Met Ala Ser Arg Ile Ile Ile Asn Glu Arg Gln Arg Leu Ile
            325                 330                 335

Asn Ser Ala Asn Gly Val Ser Ser Lys Pro Leu Gln Asn Gly Arg His
        340                 345                 350

Glu Asn Ile Glu Asn Gly Asn Val Pro Val Glu Asn Pro Glu Asp Pro
    355                 360                 365

Gln Gln Asn Gln Glu Gln Pro Pro Gln Pro Pro Pro Pro Pro Pro Glu
370                 375                 380

Pro Glu Pro Val Glu Ala Asp Phe Leu Ser Pro Phe Ser Val Pro Glu
385                 390                 395                 400

Ala Arg Gly Asp Lys Val Lys Trp Val Phe Thr Trp Pro Leu Ile Phe
                405                 410                 415

Leu Leu Cys Val Thr Ile Pro Asn Cys Ser Lys Pro Arg Trp Glu Lys
            420                 425                 430

Phe Phe Met Val Thr Phe Ile Thr Ala Thr Leu Trp Ile Ala Val Phe
        435                 440                 445

Ser Tyr Ile Met Val Trp Leu Val Thr Ile Ile Gly Tyr Thr Leu Gly
    450                 455                 460

Ile Pro Asp Val Ile Met Gly Ile Thr Phe Leu Ala Ala Gly Thr Ser
465                 470                 475                 480

Val Pro Asp Cys Met Ala Ser Leu Ile Val Ala Arg Gln Gly Leu Gly
                485                 490                 495

Asp Met Ala Val Ser Asn Thr Ile Gly Ser Asn Val Phe Asp Ile Leu
            500                 505                 510

Val Gly Leu Gly Val Pro Trp Gly Leu Gln Thr Met Val Val Asn Tyr
        515                 520                 525

Gly Ser Thr Val Lys Ile Asn Ser Arg Gly Leu Val Tyr Ser Val Val
    530                 535                 540

Leu Leu Leu Gly Ser Val Ala Leu Thr Val Leu Gly Ile His Leu Asn
545                 550                 555                 560

Lys Trp Arg Leu Asp Arg Lys Leu Gly Val Tyr Val Leu Val Leu Tyr
                565                 570                 575

Ala Ile Phe Leu Cys Phe Ser Ile Met Ile Glu Phe Asn Val Phe Thr
            580                 585                 590

Phe Val Asn Leu Pro Met Cys Arg Glu Asp Asp
        595                 600

<210> SEQ ID NO 5
<211> LENGTH: 34
<212> TYPE: DNA
<213> ORGANISM: Artificial Sequence
<220> FEATURE:
<223> OTHER INFORMATION: Description of artificial Sequence: an
      artificially synthesized primer sequence

<400> SEQUENCE: 5
caggaattcc accatggcgc tccgcgggac cctc                              34

<210> SEQ ID NO 6
<211> LENGTH: 27
<212> TYPE: DNA
<213> ORGANISM: Artificial Sequence
<220> FEATURE:
<223> OTHER INFORMATION: Description of artificial Sequence: an
      artificially synthesized primer sequence
```

```
-continued

<400> SEQUENCE: 6
ccaggtaccg cgactcagcg ctaatcg                                    27

<210> SEQ ID NO 7
<211> LENGTH: 24
<212> TYPE: DNA
<213> ORGANISM: Artificial Sequence
<220> FEATURE:
<223> OTHER INFORMATION: Description of artificial Sequence: an
      artificially synthesized primer sequence

<400> SEQUENCE: 7
atgccttggc catagtgtgc gatg                                       24

<210> SEQ ID NO 8
<211> LENGTH: 24
<212> TYPE: DNA
<213> ORGANISM: Artificial Sequence
<220> FEATURE:
<223> OTHER INFORMATION: Description of artificial Sequence: an
      artificially synthesized primer sequence

<400> SEQUENCE: 8
ctgctcacac cattggccga gttg                                       24
```